(12) United States Patent
Ignatyev et al.

(10) Patent No.: US 7,439,395 B2
(45) Date of Patent: Oct. 21, 2008

(54) PROCESS FOR THE PREPARATION OF GUANIDINIUM SALTS

(75) Inventors: Nikolai (Mykola) Ignatyev, Duisburg (DE); Urs Welz-Biermann, Heppenheim (DE); German Bissky, Wuppertal (DE); Helge Willner, Muehlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 79 days.

(21) Appl. No.: 10/588,190

(22) PCT Filed: Jan. 17, 2005

(86) PCT No.: PCT/EP2005/000389

§ 371 (c)(1),
(2), (4) Date: Aug. 2, 2006

(87) PCT Pub. No.: WO2005/075413

PCT Pub. Date: Aug. 18, 2005

(65) Prior Publication Data

US 2007/0135645 A1    Jun. 14, 2007

(30) Foreign Application Priority Data

Feb. 3, 2004  (DE) ................ 10 2004 005 404

(51) Int. Cl.
*C07C 277/00* (2006.01)
*C07C 279/00* (2006.01)

(52) U.S. Cl. .............. 564/232; 564/225; 564/230; 564/252; 548/300.1; 548/331.5

(58) Field of Classification Search .............. None
See application file for complete search history.

(56) References Cited

U.S. PATENT DOCUMENTS 4,673,632 A * 6/1987 Okamura et al. ............ 430/510
6,222,046 B1 * 4/2001 Hayashi et al. ........... 548/347.1

OTHER PUBLICATIONS

Database CAPLUS on STN, Acc. No. 1975:495825, Kalinowski et al., Organic Magnetic Resonance (1975), 7(3), p. 128-136 (abstract).*
Database CAPLUS on STN, Acc. No. 1994:271120, Akaji et al., Pept. Chem. 1992, Proc. Jpn. Symp., 2$^{nd}$ (1993), meeting date 1992, p. 51-53 (abstract).*
Database CAPLUS on STN, Acc. No. 1998:79386, Carpino et al., US 5,712,418 (Jan. 27, 1998) (abstract).*
Database CAPLUS on STN, Acc. No. 1999:529892, Isobe et al., Journal of Organic Chemistry (1999), 64(19), p. 6989-6992 (abstract).*
Database CAPLUS on STN, Acc. No. 2002:693477, Matsuo, JP 2002260966 (Sep. 13, 2002) (abstract).*
Database CAPLUS on STN, Acc. No. 1997:280902, Przybylski et al., PL 170331 (Nov. 29, 1996) (abstract).*
Database CAPLUS on STN, Acc. No. 2005:89021, Bailen et al., ES 2181554 (Feb. 16, 2003) (abstract).*
Kolomeitsev et al., Journal of Fluorine Chemistry (2000), 103(2), p. 159-161.*

* cited by examiner

*Primary Examiner*—Brian J Davis
(74) *Attorney, Agent, or Firm*—Millen, White, Zelano, Branigan, P.C.

(57) ABSTRACT

The present invention relates to a two-step process for the preparation of guanidinium salts of the formula (1), where the substituents R have a meaning indicated in Claim, and $A^-$ is a sulfonate, alkyl- or arylsulfate, hydrogensulfate, imide, methanide, carboxylate, phosphate, phosphinate, phosphonate, borate, thiocyanate, perchlorate, fluorosilicate or nitrate, and to intermediate compounds from this process.

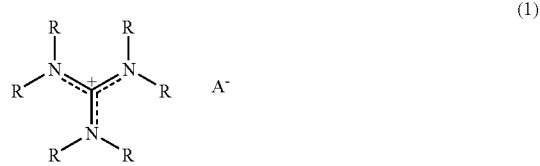

(1)

16 Claims, No Drawings

PROCESS FOR THE PREPARATION OF GUANIDINIUM SALTS

This application is a National Stage Entry of PCT/EP05/00389 filed on Jan. 17, 2005.

The invention relates to a two-step process for the preparation of guanidinium salts having an anion selected from the group sulfonate, alkyl- or arylsulfate, hydrogensulfate, imide, methanide, carboxylate, phosphate, phosphinate, phosphonate, borate, thiocyanate, perchlorate, fluorosilicate or nitrate, and to intermediate compounds in this process.

Owing to their properties, guanidinium salts are ideal compounds for use as ionic liquids, non-aqueous electrolytes, phase-transfer catalysts or surface-active substances. The area of ionic liquids is being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

Guanidinium salts can be prepared by classical processes by protonation of guanidines using strong acids or by alkylation of guanidines using alkylating reagents, such as, for example, alkyl triflate. The guanidine unit here can be obtained via a variety of methods, for example by reaction of amines with thioureas, chloroformamidinium chlorides or aminoiminomethanesulfonic acids, with the synthesis of guanidines substituted in a complex manner frequently being complicated and/or difficult (D. A. Powell, *J. Org. Chem.*, 68 (2000), 2300-2309; D. H. R. Barton, *J. Chem. Soc. Perkin Trans. I.* (1982), 2085-2090).

Guanidinium chlorides can also be obtained directly by reaction of phosgeniminium chloride with a secondary amine (T. Schlama et al, *J. Org. Chem.*, 62 (1997), 4200-4202). The conversion into guanidinium salts having anions such as, for example, hexafluorophosphate, tetrafluoroborate or bistrifluoromethanesulfonimidate corresponds to a salt exchange, as known from N. M. M Mateus et al, *Green Chemistry*, 5 (2003), 347-352. It is disadvantageous in this salt exchange that the end products are contaminated with chloride ions since the separation of the ammonium chlorides formed in parallel is often very difficult.

The object of the present invention was therefore to provide a simple and inexpensive process for the preparation of guanidinium salts which gives salts in high purity without using a guanidine as starting material.

This object is achieved by the process according to the invention.

Surprisingly, it has been found that guanidinium salts of the formula (1)

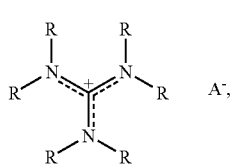

(1)

in which the substituents R in each case, independently of one another, have the meaning of hydrogen, straight-chain or branched alkyl having 1-20 C atoms, saturated, partially or fully unsaturated cycloalkyl having 3-7 C atoms, which may be substituted by alkyl groups having 1-6 C atoms, where one or more substituents R may be partially or fully substituted by halogen or partially by CN or $NO_2$ and halogen denotes F, Cl, Br or I, where up to four substituents R may be bonded to one another in pairs by a single or double bond and where a carbon atom or two non-adjacent carbon atoms of one or more substituents R may be replaced by atoms and/or atom groups selected from the group —O—, —C(O)—, —C(O)O—, —S—, —S(O)—, —$SO_2$—, —$SO_3$—, —N=, —N=N—, —NH—, —NR'—, —PR'—, —P(O)R'—, —P(O)R'—O—, —O—P(O)R'—O—, and —P(R')$_2$=N—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and $A^-$ is a sulfonate, alkyl- or arylsulfate, hydrogensulfate, imide, methanide, carboxylate, phosphate, phosphinate, phosphonate, borate, thiocyanate, perchlorate, fluorosilicate or nitrate, with the proviso that all six substituents R are not simultaneously hydrogen, can be prepared by reaction of a dihalogen compound of the formula (2)

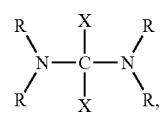

(2)

in which the substituents R have a meaning indicated for formula (1) and X denotes F, Cl or Br, with the proviso that all four substituents R are not simultaneously hydrogen, with a compound of the formula (3)

$$Kt^+ A^-  \qquad (3),$$

in which $A^-$ has a meaning indicated for formula (1) and $Kt^+$ can be a proton, $R''_3Si$, an alkali or alkaline earth metal cation, an ammonium cation, a phosphonium cation or a cation from group 11 or 12, where R" in each case, independently of one another, denotes phenyl or a linear or branched alkyl group having 1-6 C atoms, which may be substituted by phenyl, and subsequent reaction of the resultant compound of the formula (4)

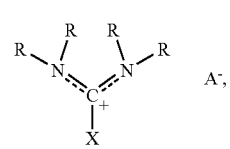

(4)

where the substituents R, X and $A^-$ have a meaning indicated for formula (1) or (2), with a compound of the formula (5)

(5)

where the substituents R have a meaning indicated for formula (1) and M denotes hydrogen, R"$_3$Si, an alkali or alkaline earth metal and R" in each case, independently of one another, denotes phenyl or a linear or branched alkyl group having 1-6 C atoms, which may be substituted by phenyl.

Suitable substituents R of the guanidinium cation here, besides hydrogen, are: $C_1$- to $C_{20}$-alkyl groups, in particular alkyl groups having 1, 2, 3, 4, 5, 6, 7, 8, 9, 10, 11 or 12 C atoms, and saturated or unsaturated, i.e. also aromatic, $C_3$- to $C_7$-cycloalkyl groups, which may be substituted by $C_1$- to $C_6$-alkyl groups, in particular phenyl. The six substituents R of the guanidinium cation here may be identical or different, where all six substituents must not be equal to hydrogen.

The $C_1$-$C_6$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl or hexyl. Optionally difluoromethyl, trifluoromethyl, pentafluoroethyl, heptafluoropropyl or nonafluorobutyl.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, CN or $NO_2$.

Furthermore, the substituents R may contain one or two non-adjacent heteroatoms or atom groups selected from the group O, C(O), C(O)O, S, S(O), $SO_2$, $SO_2O$, N, N=N, NH, NR', PR', P(O)R', P(O)R'O, OP(O)R'O and PR'$_2$=N, where R' can be a non-, partially or perfluorinated $C_1$- to $C_6$-alkyl, saturated or partially unsaturated $C_3$- to $C_7$-cycloalkyl, unsubstituted or substituted phenyl or an unsubstituted or substituted heterocycle.

The phenyl group here may be substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR'$_2$, $SO_2OR'$, $SO_2X'$, $SO_2NR'_2$, $SO_3H$ or NHC(O)R', where X' denotes F, Cl or Br and R' has a meaning indicated above, for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p- (trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

Heterocycle is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR'$_2$, $SO_2OR'$, $SO_2X'$, $SO_2NR'_2$, $SO_3H$ or NHC(O)R', where X' and R' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Without restricting generality, examples of substituents R of the guanidinium cation are:

—$CH_3$, —$C_2H_5$, —$C_3H_7$, —$CH(CH_3)_2$, —$C_4H_9$, —$C(CH_3)_3$, —$C_5H_{11}$, —$C_6H_{13}$, —$C_7H_{15}$, —$C_8H_{17}$, —$C_9H_{19}$, —$C_{10}H_{21}$, —$C_{12}H_{25}$, —$C_{20}H_{41}$, —$OCH_3$, —$OCH(CH_3)_2$, —$CH_2OCH_3$, —$C_2H_4OCH(CH_3)_2$, —$SCH_3$, —$SCH(CH_3)_2$, —$C_2H_4SC_2H_5$, —$C_2H_4SCH(CH_3)_2$, —S(O)$CH_3$, —$SO_2CH_3$, —$SO_2C_2H_5$, —$SO_2C_3H_7$, —$SO_2CH(CH_3)_2$, —$CH_2SO_2CH_3$, —$CH_2N(H)C_2H_5$, —$C_2H_4N(H)C_2H_5$, —$CH_2N(CH_3)CH_3$, —CN, —$C_2H_4N(CH_3)CH_3$, —$N(CH_3)_2$, —$N(CH_3)C_3H_5$, —$N(CH_3)CF_3$, —O—$C_4H_8$—O—$C_4H_9$, —S—$C_2H_4$—N($C_4H_9)_2$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3FH_6$, —$CH_2C_3F_7$, —$C(CFH_2)_3$, —$CH_2C(O)OH$, —$CH_2C(O)CH_3$, —$CH_2C(O)C_2H_5$, —$CH_2C(O)OCH_3$, $CH_2C(O)$ $OC_2H_5$, —$C(O)CH_3$, —$C(O)OCH_3$,

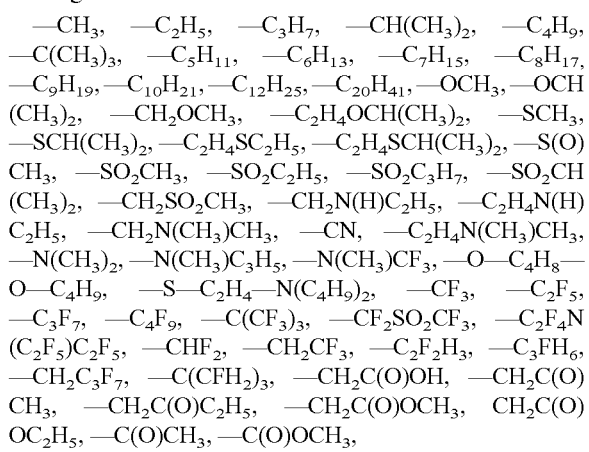

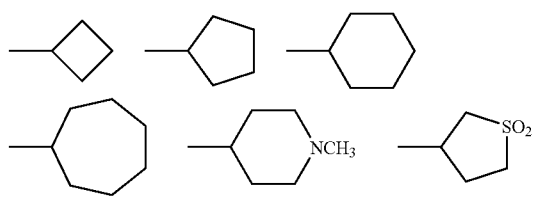

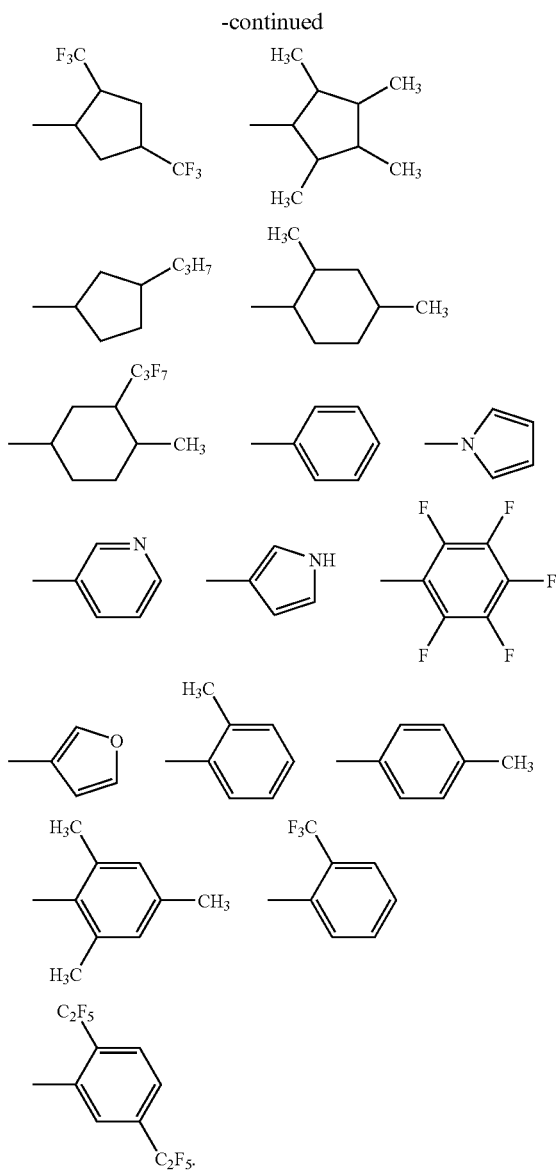

Up to four substituents R may also be bonded in pairs in such a way that mono-, bi- or polycyclic cations are formed.

Without restricting generality, examples of such guanidinium cations are:

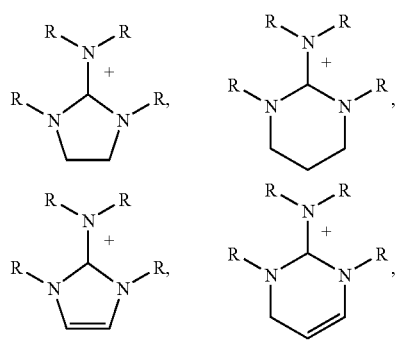

or, where the substituents R can have a meaning indicated above or a particularly preferred meaning. If desired, the carbocycles or heterocycles of the guanidinium cations indicated above may also be substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR'$_2$, $SO_2$OR', $SO_2$NR'$_2$, $SO_2$X', $SO_3$H or NHC(O)R', where X' and R' have a meaning indicated above, substituted or unsubstituted phenyl or an unsubstituted or substituted heterocycle.

Dihalogen compounds of the formula (2)

(2)

in which the substituents R have a meaning indicated for formula (1) or a preferred meaning and X denotes F, Cl or Br, with the proviso that all four substituents R are not simultaneously hydrogen, are generally commercially available or can be prepared by synthetic methods as are known from the literature, for example in the standard works, such as Houben-Weyl, Methoden der organischen Chemie [Methods of Organic Chemistry], Georg-Thieme-Verlag, Stuttgart or from K. Ohno et al., *Heterocycles*, 59 (2003), 317-322, A. A. Kolomeitsev et al., *J. Fluorine Chem.*, 103 (2000),159-162 or H. Wittmann et al, *Eur. J. Inorganic. Chem.*, 8 (2001), 1937-1948. Use can also be made here of variants known per se which are not mentioned here in greater detail.

Particular preference is given to compounds of the formula (2) in which X denotes F or Cl, very particular preference is given to compounds of the formula (2) in which X denotes Cl.

The compounds of the formula (3)

$$Kt^+ A^- \qquad (3),$$

in which A⁻ has a meaning indicated for formula (1) and Kt⁺ can be a proton, R"₃Si, an alkali or alkaline earth metal cation, an ammonium cation, a phosphonium cation or a cation from group 11 or 12, where R" in each case, independently of one another, denotes phenyl or a linear or branched alkyl group having 1-6 C atoms, which may be substituted by phenyl, are generally likewise commercially available or can be prepared by synthetic methods as are known from the literature, for example in the standard works, such as Houben-Weyl, Methoden der organischen Chemie [Methods of Organic Chemistry], Georg-Thieme-Verlag, Stuttgart, Encyclopedia of Reagents for Organic Synthesis, Ed. Leo A. Paquette, John Wiley and Sons Ltd, 1995, EP 0929558 B1 or U.S. Pat. No. 6,423,454 for fluoroalkylphosphates, EP 1174941, EP 1205480 or EP 1229038 for fluoroalkylborates.

Use can also be made here of variants known per se which are not mentioned here in greater detail.

Kt⁺ is, for example, $NH_4^+$, $H^+$, $Li^+$, $Na^+$, $K^+$, $Rb^+$, $Mg^{2+}$, $Ca^{2+}$, $Ba^{2+}$, $Cu^+$, $Cu^{2+}$, $Ag^+$, $Zn^{2+}$, $Cd^{2+}$, $Hg^+$ or $Hg^{2+}$, particularly preferably $NH_4^+$, $H^+$, $Li^+$, $Na^+$, $K^+$, $Rb^+$ or $Ca^{2+}$, where the charge in the respective salt form of the formula (3) is balanced. For a divalent cation, two monovalent anions of the formula A⁻ are required for charge balancing. For charge balancing of a divalent anion, two monovalent cations Kt⁺ are required. The proviso of charge balancing naturally also applies to compounds of the formula (1) and formula (4).

The anion A⁻ is selected from the group sulfonate, alkyl- or arylsulfate, hydrogensulfate, imide, methanide, carboxylate, phosphate, phosphinate, phosphonate, borate, thiocyanate, perchlorate, fluorosilicate or nitrate.

Preference is given to the selection of anions A⁻ of the formulae $[R^1OSO_3]^-$, $[R^1SO_3]^-$, $[R^FSO_3]^-$, $[(FSO_2)_2N]^-$, $[(R^FSO_2)_2N]^-$, $[(R^FSO_2)(R^FCO)N]^-$, $[(R^FSO_2)_3C]^-$, $[(FSO_2)_3C]^-$, $[R^1CH_2C(O)O]^-$, $[R^FC(O)O]^-$, $[P(C_nF_{2n+1-m}H_m)_yF_{6-y}]^-$, $[P(C_6F_5)_yF_{6-y}]^-$, $[(R^1O)_2P(O)O]^-$, $[R^1_2P(O)O]^-$, $[R^1P(O)O_2]^{2-}$, $[R^F_2P(O)O]^-$, $[R^FP(O)O_2]^{2-}$, $[BF_{4-z}R^F_z]^-$, $[BF_{4-z}(CN)_z]^-$, $[B(C_6F_5)_4]^-$, $[B(OR^1)_4]^-$, $[N(CN)_2]^-$, $[C(CN)_3]^-$, $[N(CF_3)_2]^-$, $[HSO_4]^-$, $[SiF_6]^{2-}$, $[ClO_4]^-$, $[SCN]^-$ and $[NO_3]^-$, in which the substituents $R^F$ in each case, independently of one another, have the meaning of perfluorinated and straight-chain or branched alkyl having 1-20 C atoms, perfluorinated and straight-chain or branched alkenyl having 2-20 C atoms and one or more double bonds, perfluorinated and saturated, partially or fully unsaturated cycloalkyl having 3-7 C atoms, which may be substituted by perfluoroalkyl groups, where the substituents $R^F$ may be bonded to one another in pairs by a single or double bond and where a carbon atom or two non-adjacent carbon atoms of the substituent $R^F$ which are not in the α-position to the heteroatom may be replaced by atoms and/or atom groups selected from the group —O—, —C(O)—, —S—, —S(O)—, —SO₂—, —N═, —N═N—, —NR'—, —PR'— and —P(O)R'—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle, in which the substituents $R^1$ in each case, independently of one another, have the meaning of straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where the substituents $R^1$ may be partially substituted by CN, NO₂ or halogen and halogen denotes F, Cl, Br or I, where the substituents $R^1$ may be bonded to one another in pairs by a single or double bond and where a carbon atom or two non-adjacent carbon atoms of the substituent $R^1$ which are not in the α-position to the heteroatom may be replaced by atoms and/or atom groups selected from the group —O—, —C(O)—, —C(O)O—, —S—, —S(O)—, —SO₂—, —SO₃—, —N═, —N═N—, —NH—, —NR'—, —PR'—, —P(O)R'—, P(O)R'O—, OP(O)R'O—, —PR'₂═N—, —C(O)NH—, —C(O)NR'—, —SO₂NH— or —SO₂NR'—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and the variables n denotes 1 to 20, m denotes 0, 1, 2 or 3, y denotes 0, 1, 2, 3, or 4, z denotes 0, 1, 2, 3 or 4.

Suitable organic groups $R^F$ or $R^1$ of the anion here are: $C_1$- to $C_{20}$-, in particular $C_1$- to $C_{12}$-alkyl groups, $C_2$- to $C_{20}$-, in particular $C_2$- to $C_{12}$-alkenyl groups or saturated or unsaturated, i.e. also aromatic, $C_3$- to $C_7$-cycloalkyl groups, which may be substituted by $C_1$- to $C_6$-alkyl groups, in particular phenyl. Suitable organic groups for $R^1$ are also $C_2$- to $C_{20}$-, in particular $C_2$- to $C_{12}$-alkynyl groups.

A straight-chain or branched alkenyl having 2 to 20 C atoms, in which a plurality of double bonds may also be present, is, for example, vinyl, allyl, 2- or 3-butenyl, isobutenyl, sec-butenyl, furthermore 4-pentenyl, isopentenyl, hexenyl, heptenyl, octenyl, —C₉H₁₇, —C₁₀H₁₉ to —C₂₀H₃₉; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —C₉H₁₅, —C₁₀H₁₇ to —C₂₀H₃₇, preferably ethynyl, 1- or 2-propynyl, 2- or 3-butynyl, 4-pentynyl, 3-pentynyl or hexynyl.

The groups $R^F$ are perfluorinated, i.e. all carbon atoms are saturated not with hydrogen, but instead with fluorine atoms. The groups $R^1$ may be partially substituted by halogen atoms, in particular by F and/or Cl, CN or NO₂.

In the case where a plurality of $R^F$ or $R^1$ are present in an anion, these may also be bonded in pairs by single or double bonds in such a way that mono- or bicyclic anions are formed.

Furthermore, the substituents $R^F$ may contain one or two atoms or atom groups, which are not adjacent to one another and are not in the α-position to the heteroatom, selected from the group —O—, —C(O)—, —S—, —S(O)—, —SO₂—, —N═, —N═N—, —NR'—, —PR'— and —P(O)R'—, where R' can be a non-, partially or perfluorinated $C_1$- to $C_6$-alkyl, $C_3$- to $C_7$-cycloalkyl, an unsubstituted or substituted phenyl, including —C₆F₅, or an unsubstituted or substituted heterocycle.

Furthermore, the substituents $R^1$ may contain one or two atoms or atom groups, which are not adjacent to one another and are not in the α-position to the heteroatom, selected from the group —O—, —C(O)—, —C(O)O—, —S—, —S(O)—, —SO₂—, —SO₃—, —N=, —N=N—, —NH—, —NR'—, —PR'—, —P(O)R'—, P(O)R'O—, OP(O)R'O—, —PR'₂=N—, —C(O)NH—, —C(O)NR'—, —SO₂NH— or —SO₂NR'—, where R' can be a non—, partially or perfluorinated C₁ to C₆-alkyl, C₃- to C₇-cycloalkyl, an unsubstituted or substituted phenyl, including —C₆F₅, or an unsubstituted or substituted heterocycle.

Without restricting generality, examples of substituents R¹ or R^F of the anion are:

—CH₃, —C₂H₅, —C₃H₇, —CH(CH₃)₂, —C₄H₉, —C(CH₃)₃, —C₅H₁₁, —C₆H₁₃, —C₇H₁₅, —C₈H₁₇, —C₉H₁₉, —C₁₀H₂₁, —C₁₂H₂₅, —C₂₀H₄₁, —CH₂OCH(CH₃)₂, —CH₂OCH₃, —C₂H₄OCH(CH₃)₂, —CH₂SCH₃, —CH₂SCH(CH₃)₂, —C₂H₄SC₂H₅, —C₂H₄SCH(CH₃)₂, —CH₂S(O)CH₃, —CH₂SO₂CH₃, —C₂H₄SO₂C₂H₅, —C₂H₄SO₂C₃H₇, —CH₂SO₂CH(CH₃)₂, —CH₂SO₂CH₃, —CH₂OSO₂CH₃, —CH₂N(H)C₂H₅, —C₂H₄N(H)C₂H₅, —CH₂N(CH₃)CH₃, —C₂H₄N(CH₃)CH₃, —CH₂N(CH₃)₂, —C₂H₄N(CH₃)C₃H₅, —C₂H₄O—C₄H₈—O—C₄H₉, —C₂H₄S—C₂H₄—N(C₄H₉)₂, —CHF₂, —CH₂CF₃, —C₂F₂H₃, —C₃FH₆, —CH₂C₃F₇, —C(CFH₂)₃, —CH₂C(O)OH, —CH₂C(O)CH₃, —CH₂C(O)C₂H₅, —CH₂C(O)OCH₃, CH₂C(O)OC₂H₅, —C(O)CH₃, —C(O)OCH₃, —CH=CH₂, —C(CH₃)=CHCH₃, —CH₂CH=CHCH₃, —CH=CHN(CH₃)CH₃,

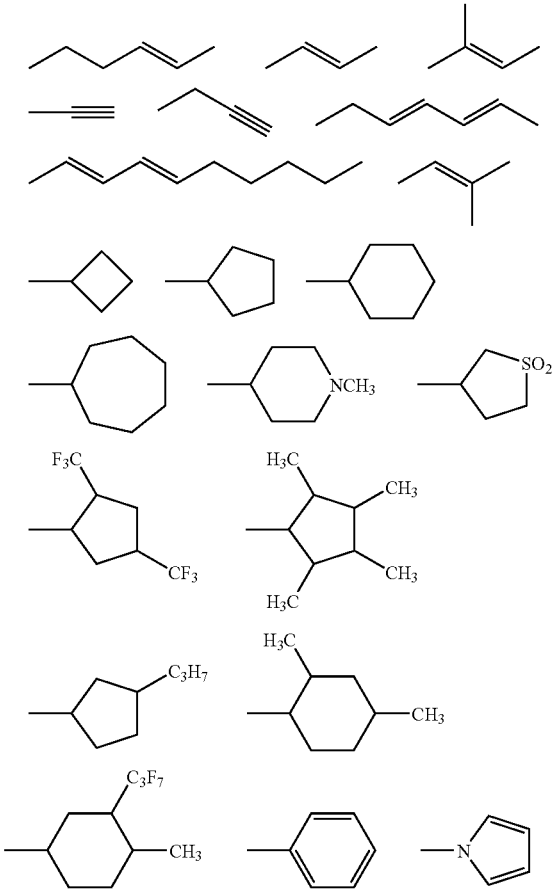

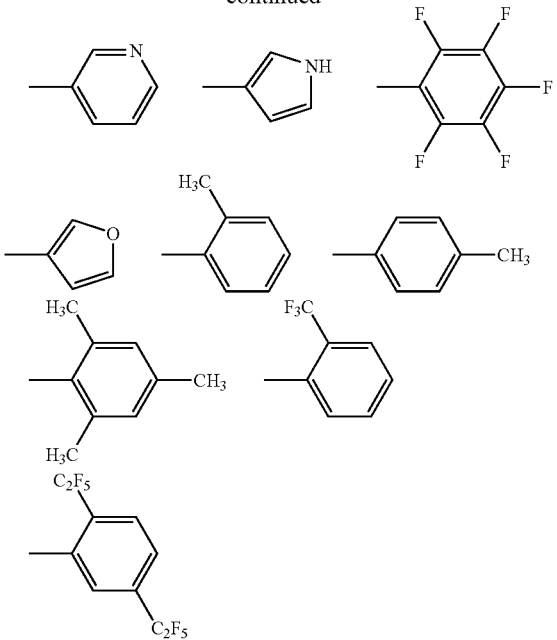

—CF₃, —C₂F₅, —C₃F₇, —C₄F₉, —C(CF₃)₃, —CF₂N(CF₃)CF₃, —CF₂OCF₃, —CF₂S(O)CF₃, —CF₂SO₂CF₃, —C₂F₄N(C₂F₅)C₂F₅, CF=CF₂, —C(CF₃)=CFCF₃, —CF₂CF=CFCF₃, —CF=CFN(CF₃)CF₃ or —CF₂SO₂F.

Without restricting generality, some examples of anions A⁻ are indicated below: [CH₃OSO₃]⁻, [C₂H₅OSO₃]⁻, [C(CN)₃]⁻, [CH₃SO₃]⁻, [C₈H₁₇SO₃]⁻, [CH₃C₆H₄SO₃]⁻, [CF₃SO₃]⁻, [C₂H₅SO₃]⁻, [CF₃CF₂SO₃]⁻, [(CF₃SO₂)₂N]⁻, [(FSO₂)₂N]⁻, [(CF₃SO₂)(CF₃CO)N]⁻, [(C₂F₅SO₂)(CF₃CO)N]⁻, [(C₂F₅SO₂)₂N]⁻, [(CF₃SO₂)₃C]⁻, [(C₂F₅SO₂)₃C]⁻, [(FSO₂)₃C]⁻, [CH₃C(O)O]⁻, [C₂H₅C(O)O]⁻, [CF₃C(O)O]⁻, [CF₃CF₂C(O)O]⁻, [PF₆]⁻, [P(C₂F₅)₃F₃]⁻, [P(C₄F₉)₃F₃]⁻, [P(CF₃)₃F₃]⁻, [P(C₂F₄H)(CF₃)₂F₃]⁻, [P(C₂F₃H₂)₃F₃]⁻, [P(C₂F₅)(CF₃)₂F₃]⁻, [P(C₆F₅)₃F₃]⁻, [P(C₃F₇)₃F₃]⁻, [P(C₂F₅)₂F₄]⁻, [(HO)₂P(O)O]⁻, [(CH₃O)₂P(O)O]⁻, [(C₂H₅O)₂P(O)O]⁻, [(C₂F₅)₂P(O)O]⁻, [(C₂F₅)P(O)O₂]⁻, [P(C₆F₅)₂F₄]⁻, [(CH₃)₂P(O)O]⁻, [CH₃P(O)O₂]²⁻, [(CF₃)₂P(O)O]⁻, [CF₃P(O)O₂]²⁻, [BF₄]⁻, [BF₃(CF₃)]⁻, [BF₂(C₂F₅)₂]⁻, [BF₃(C₂F₅)]⁻, [BF₂(CF₃)₂]⁻, [B(C₂F₅)₄]⁻, [BF₃(CN)]⁻, [BF₂(CN)₂]⁻, [B(CN)₄]⁻, [B(OCH₃)₄]⁻, [B(CF₃)₄]⁻, [B(OCH₃)₂(OC₂H₅)₂]⁻, [B(O₂C₂H₄)₂]⁻, [B(O₂C₂H₂)₂]⁻, [B(O₂C₆H₄)₂]⁻, [N(CN)₂]⁻, [N(CF₃)₂]⁻, [HSO₄]⁻, [ClO₄]⁻, [SiF₆]⁻, [SCN]⁻ or [NO₃]⁻.

Preferred anions A⁻ are [CH₃OSO₃]⁻, [CH₃SO₃]⁻, [CF₃SO₃]⁻, [C₈H₁₇SO₃]⁻, [CH₃C₆H₄SO₃]⁻, [C₂F₅SO₃]⁻, [PF₆]⁻, [(C₂F₅)₃PF₃]⁻, [(C₂F₅)₂PF₄]⁻, [(C₄F₉)₃PF₃]⁻, [(C₃F₇)₃PF₃]⁻, [(HO)₂P(O)O]⁻, [(C₂F₅)₂P(O)O]⁻, [(CH₃O)₂P(O)O]⁻, [(C₂F₅)P(O)O₂]²⁻, [BF₄]⁻, [B(CN)₄]⁻, [B(CF₃)₄]⁻, [B(C₂F₅)F₃]⁻, [N(CN)₂]⁻, [N(CF₃)₂]⁻, [N(SO₂CF₃)₂]⁻, [HSO₄]⁻, [SiF₆]²⁻, [ClO₄]⁻, [SCN]⁻ or [NO₃]⁻.

Preferred compounds of the formula (3) are Na[OSO₂OCH₃], Na[SO₃CH₃], HSO₃CH₃, Na[SO₃CF₃], HSO₃CF₃, Ca[SO₃CF₃]₂, (CH₃)₃Si[SO₃CF₃], CH₃C₆H₄SO₃H, Na[C₂H₅SO₃], C₂H₅SO₃H, Na[CF₃CF₂SO₃], C₂F₅SO₃H, Li[(CF₃SO₂)₂N], H[(CF₃SO₂)₂N], Li[(C₂F₅SO₂)₂N], Li[(CF₃SO₂)₃C], H[(CF₃SO₂)₃C], Li[(C₂F₅SO₂)₃C], K[(FSO₂)₃C], Na[CH₃C(O)O], CF₃COOH, Na[C₂H₅C(O)O], H[CF₃CF₂C(O)O], H[PF₆], H[P(C₂F₅)₃F₃], H[P(CF₃)₃F₃], H[P(C₂F₄H)(CF₃)₂F₃], H[P $(C_2F_3H_2)_3F_3]$, $H[P(C_2F_5)(CF_3)_2F_3]$, $H[P(C_6F_5)_3F_3]$, $H[P(C_3F_7)_3F_3]$, $H[P(C_2F_5)_2F_4]$, $H_3PO_4$, $Na[(CH_3O)_2P(O)O]$, $H[(C_2F_5)_2P(O)O]$, $Li_2[(C_2F_5)P(O)O_2]$, $H_2[(C_2F_5)P(O)O_2]$, $H[P(C_6F_5)_2F_4]$, $Na[(CH_3)_2P(O)O]$, $Na_2[CH_3P(O)O_2]$, $H[(CF_3)_2P(O)O]$, $H_2[CF_3P(O)O_2]$, $Na[BF_4]$, $NH_4[BF_4]$, $K[BF_3(CF_3)]$, $K[BF_2(C_2F_5)_2]$, $K[BF_3(C_2F_5)]$, $K[BF_2(CF_3)_2]$, $K[B(C_2F_5)_4]$, $K[BF_3(CN)]$, $K[BF_2(CN)_2]$, $Na[B(CN)_4]$, $K[B(CN)_4]$, $Li[B(OCH_3)_4]$, $K[B(CF_3)_4]$, $Li[B(OCH_3)_2(OC_2H_5)_2]$, $Li[B(O_2C_2H_4)_2]$, $Li[B(O_2C_2H_2)_2]$, $Li[B(O_2C_6H_4)_2]$, $Ag[C(CN)_3]$, $Na[N(CN)_2]$, $Rb[N(CF_3)_2]$, $Na[SO_4CH_3]$, $Na[HSO_4]$, $[H_2SO_4]$, $[H_2SiF_6]$, $Li[ClO_4]$, $Na[ClO_4]$, $Na[SCN]$ or $H[NO_3]$.

Particularly preferred compounds of the formula (3) are $H[P(C_2F_5)_3F_3]*5H_2O$, $Li[(CF_3SO_2)_2N]$, $H[SO_3CF_3]$, $Ca[(SO_3CF_3)_2]$, $Na[OSO_2OCH_3]$, $(CH_3)_3Si[SO_3CF_3]$, $Na[ClO_4]$, $H[SO_3C_6H_4CH_3]$, $H[(CF_3SO_2)_2N]$, $H_3PO_4$, $Na[(CH_3O)_2P(O)O]$, $H[O(O)P(C_2F_5)_2]$, $Rb[N(CF_3)_2]$, $Na[SO_4CH_3]$ or $H_2SO_4$.

The reaction of the dihalogen compounds of the formula (2) with compounds of the formula (3) can advantageously be carried out in water, in which case temperatures of 0°-150° C., preferably 0°-40° C. are suitable. The reaction is particularly preferably carried out at room temperature.

However, the reaction can alternatively also be carried out in organic solvents at temperatures between −50° and 150° C. Suitable solvents here are water-miscible solvents, such as, for example, dimethoxyethane, acetonitrile, acetone, tetrahydrofuran, dimethylformamide, dimethyl sulfoxide, dioxane, propionitrile, methanol, ethanol or isopropanol, or mixtures with one another or with water. Acetonitrile is a preferred organic solvent. The reaction is preferably carried out at 0°-100°, particularly preferably at 10°-70° C., very particularly preferably at room temperature.

The reaction of the dihalogen compounds of the formula (2) with compounds of the formula (3) can also be carried out without the use of solvents, to be precise at temperatures at which the dihalogen compound of the formula (2) is liquid.

It is possible to carry out the reaction under a protective-gas atmosphere, which is preferred for oxidation-sensitive starting materials. In accordance with the invention, the compounds of the formula (2) are reacted with compounds of the formula (3) in equimolar amounts or with an excess of the compound of the formula (3). An excess of 5 to 20% of compound of the formula (3) is preferably employed. For the reaction of the compounds of the formula (3) which have $[N(CF_3)_2]^-$ as counterion with dichloro or dibromo compounds of the formula (2), it is advantageous to employ the compound of the formula (3) in at least twice the molar amount.

The compounds of the formula (4)

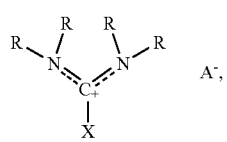

(4)

where the substituents R, X and A⁻ have one of the meanings indicated above or meanings indicated as preferred, emanating from this first reaction can be isolated with very good yield, generally above 80%, preferably above 90%. It is advantageous here that the separation of the inorganic salts KtX formed is straightforward and the compounds of the formula (4) are not contaminated by halogen anions X⁻. The subsequent reaction of the compounds of the formula (4) with ammonia, alkyl- or arylamines or -amides of the formula (5) is driven by the high electrophilicity of the carbocation.

The compounds of the formula (5)

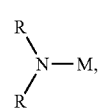

(5)

where the substituents R have a meaning indicated for formula (1) or indicated as preferred and M denotes hydrogen, R"₃Si, an alkali or alkaline earth metal and R" in each case, independently of one another, denotes phenyl or a linear or branched alkyl group having 1-6 C atoms, which may be substituted by phenyl, are generally likewise commercially available or can be prepared by synthetic methods as are known from the literature, for example in the standard works, such as Houben-Weyl, Methoden der organischen Chemie [Methods of Organic Chemistry], Georg-Thieme-Verlag, Stuttgart, or the Encyclopedia of Reagents for Organic Synthesis. Ed. Leo A. Paquette, John Wiley and Sons Ltd., 1995. Use can also be made here of variants known per se, which are not mentioned here in greater detail.

The substituents R in formula (5) are in each case, independently of one another, preferably hydrogen, straight-chain or branched alkyl having 1-20 C atoms or saturated, partially or fully unsaturated cycloalkyl having 3-7 C atoms, which may be substituted by alkyl groups having 1-6 C atoms.

Preferred compounds of the formula (5) are ammonia, methylamine, dimethylamine, ethylamine, diethylamine, butylamine, dibutylamine, cyclohexylamine, dicyclohexylamine, lithium dimethylamide, N,N-dimethyltrimethylsilylamine or N,N-diethyltrimethylsilylamine. Particularly preferred compounds of the formula (5) are ethylamine, dimethylamine, diethylamine, dibutylamine, dicyclohexylamine, N,N-diethyltrimethylsilylamine, N,N-dimethyltrimethylsilylamine or lithium dimethylamide.

The second reaction of the chloroformamidinium salts of the formula (4) with compounds of the formula (5) can be carried out at a temperature at which at least one of the two starting materials is liquid. The use of solvents is then advantageously superfluous. The reaction is preferably carried out at temperatures of 15°-100° C., particularly preferably at 50°-70° C. or room temperature.

However, the reaction can alternatively also be carried out in organic solvents at temperatures between −5° and 150° C. Suitable solvents here are water-miscible solvents, such as, for example, dimethoxyethane, acetonitrile, acetone, tetrahydrofuran, dimethylformamide, dimethyl sulfoxide, dioxane, propionitrile, methanol, ethanol or isopropanol, or mixtures with one another or with water. In the case of reactions with a silylamine, a water-immiscible organic solvent is preferably used, for example dichloromethane or chloroform, preferably chloroform. The reaction is preferably carried out at 10°-70° C., particularly preferably at 40°-50° C. or room temperature. However, the reaction can likewise advantageously be carried out in water, in which case temperatures of 0°-150° C. are suitable. Reactions in water are preferably carried out at room temperature.

It is possible to carry out the reaction under a protective-gas atmosphere, which is preferred for oxidation-sensitive starting materials. It is likewise carried out at atmospheric pressure, where the reaction with, for example, ammonia, methylamine or dimethylamine, i.e. gaseous or readily volatile compounds of the formula (5), is advantageously carried out in closed vessels. Step 2 of the process according to the invention can also be carried out under pressure, where a pressure of up to 50 bar may be advantageous.

In accordance with the invention, the compounds of the formula (4) are reacted with compounds of the formula (5) in equimolar amount. An excess of compounds of the formula (5) may be advantageous.

The guanidinium salts of the formula (1) emanating from this second step, as described above, can be isolated with very good yield, generally above 80%, preferably above 90%.

The process according to the invention is preferably used for the preparation of guanidinium salts of the general formula (1)

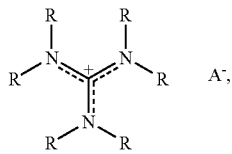

(1)

in which the substituents R in each case, independently of one another, denote hydrogen or a straight-chain or branched alkyl group having 1-12 C atoms, in particular 1, 2, 3, 4, 5, 6, 7 or 8 C atoms, with the proviso that all six substituents R are not hydrogen, or at least two substituents R are bonded to one another by single or double bonds in such a way that a monocyclic cation is formed and the counteranion $A^-$ has one of the meanings indicated for formula (3) or a preferred or very preferred meaning.

The process according to the invention is very particularly preferably used for the preparation of guanidinium salts of the formula (1) in which the substituents R in each case, independently of one another, denote methyl, ethyl, n-propyl, isopropyl, n-butyl, tert-butyl, sec-butyl, n-hexyl, n-octyl, cyclohexyl or phenyl or two substituents R are bonded to one another in such a way that an imidazolidinium cation is formed and the counteranion $A^-$ has one of the meanings indicated for formula (3) or a preferred or very preferred meaning.

The intermediate compounds of the formula (4) obtained after the first step of the process according to the invention are likewise, owing to their properties, suitable compounds for use as ionic liquids.

The invention therefore likewise relates to the intermediate compounds of the formula (4)

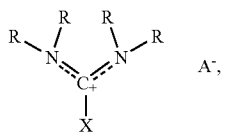

(4)

in which the substituents R in each case, independently of one another, have the meaning of hydrogen, straight-chain or branched alkyl having 1-20 C atoms, saturated, partially or fully unsaturated cycloalkyl having 3-7 C atoms, which may be substituted by alkyl groups having 1-6 C atoms, where one or more substituents R may be partially or fully substituted by halogen or partially by CN or $NO_2$ and halogen denotes F, Cl, Br or I, where up to four substituents R may be bonded to one another in pairs by a single or double bond and where a carbon atom or two non-adjacent carbon atoms of one or more substituents R may be replaced by atoms and/or atom groups selected from the group —O—, —C(O)—, —C(O)O—, —S—, —S(O)—, —$SO_2$—, —$SO_3$—, —N=, —N=N—, —NH—, —NR'—, —PR'—, —P(O)R'—, —P(O)R'—O—, —O—P(O)R'—O—, and —P(R')$_2$=N—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle, X denotes F, Cl or Br, with the proviso that all four substituents R are not simultaneously hydrogen and $A^-$ is selected from the group $[R^1OSO_3]^-$, $[R^1SO_3]^-$, $[R^FSO_3]^-$, $[(FSO_2)_2N]^-$, $[(R^FSO_2)_2N]^-$, $[(R^FSO_2)(R^FCO)N]^-$, $[(R^FSO_2)_3C]^-$, $[(FSO_2)_3C]^-$, $[R^1CH_2C(O)O]^-$, $[R^FC(O)O]^-$, $[P(C_nF_{2n+1-m}H_m)_yF_{6-y}]^-$, $[P(C_6F_5)_xF_{6-y}]^-$, $[(R^1O)_2P(O)O]^-$, $[R^1_2P(O)O]^-$, $[R^1P(O)O_2]^{2-}$, $[R^F_2P(O)O]^-$, $[R^FP(O)O_2]^{2-}$, $[BF_{4-z}R^F_z]^-$, $[BF_{4-z}(CN)_z]^-$, $[B(C_6F_5)_4]^-$, $[B(OR^1)_4]^-$, $[N(CN)_2]^-$, $[C(CN)_3]^-$, $[N(CF_3)_2]^-$, $[HSO_4]^-$, $[SiF_6]^{2-}$, $[ClO_4]^-$, $[SCN]^-$ and $[NO_3]^-$, where $[CF_3SO_3]^-$ is excepted and in which the substituents $R^F$ in each case, independently of one another, have the meaning of perfluorinated and straight-chain or branched alkyl having 1-20 C atoms, perfluorinated and straight-chain or branched alkenyl having 2-20 C atoms and one or more double bonds, perfluorinated and saturated, partially or fully unsaturated cycloalkyl having 3-7 C atoms, which may be substituted by perfluoroalkyl groups, where the substituents $R^F$ may be bonded to one another in pairs by a single or double bond and where a carbon atom or two non-adjacent carbon atoms of the substituent $R^F$ which are not in the α-position to the heteroatom may be replaced by atoms and/or atom groups selected from the group —O—, —C(O)—, —S—, —S(O)—, —$SO_2$—, —N=, —N=N—, —NR'—, —PR'— and —P(O)R'—, where R' denotes non—fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle, in which the substituents $R^1$ in each case, independently of one another, have the meaning of straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where the substituents $R^1$ may be partially substituted by CN, $NO_2$ or halogen and halogen denotes F, Cl, Br or I, where the substituents $R^1$ may be bonded to one another in pairs by a single or double bond and where a carbon atom or two non-adjacent carbon atoms of the substituent $R^1$ which are not in the α-position to the heteroatom may be replaced by atoms and/or atom groups selected from the group —O—, —C(O)—, —C(O)O—, —S—, —S(O)—, —SO$_2$—, —SO$_3$—, —N=, —N=N—, —NH—, —NR'—, —PR'—, —P(O)R'—, P(O)R'O—, OP(O)R'O—, —PR'$_2$=N—, —C(O)NH—, —C(O)NR'—, —SO$_2$NH— or —SO$_2$NR'—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and the variables n denotes 1 to 20, m denotes 0, 1, 2 or 3, y denotes 1, 2, 3 or 4 and z denotes 1, 2, 3 or 4.

Preference is given to compounds of the formula (4) in which the substituents R denote hydrogen or a straight-chain or branched alkyl group having 1-12 C atoms, in particular 1, 2, 3, 4, 5, 6, 7 or 8 C atoms, with the proviso that all four substituents R are not hydrogen, or at least two substituents R are bonded to one another by single or double bonds in such a way that a monocyclic cation is formed and the counteranion A$^-$ denotes [CH$_3$OSO$_3$]$^-$, [C$_2$H$_5$OSO$_3$]$^-$, [C(CN)$_3$]$^-$, [CH$_3$SO$_3$]$^-$, [C$_8$H$_{17}$SO$_3$]$^-$, [CH$_3$C$_6$H$_4$SO$_3$]$^-$, [CF$_3$SO$_3$]$^-$, [C$_2$F$_5$SO$_3$]$^-$, [CF$_3$CF$_2$SO$_3$]$^-$, [(CF$_3$SO$_2$)$_2$N]$^-$, [(FSO$_2$)$_2$N]$^-$, [(CF$_3$SO$_2$)(CF$_3$CO)N]$^-$, [(C$_2$F$_5$SO$_2$)(CF$_3$CO)N]$^-$, [(C$_2$F$_5$SO$_2$)$_2$N]$^-$, [(CF$_3$SO$_2$)$_3$C]$^-$, [(C$_2$F$_5$SO$_2$)$_3$C]$^-$, [(FSO$_2$)$_3$C]$^-$, [CH$_3$C(O)O]$^-$, [C$_2$H$_5$C(O)O]$^-$, [CF$_3$C(O)O]$^-$, [CF$_3$CF$_2$C(O)O]$^-$, [PF$_6$]$^-$, [P(C$_2$F$_5$)$_3$F$_3$]$^-$, [P(C$_4$F$_9$)$_3$F$_3$]$^-$, [P(CF$_3$)$_3$F$_3$]$^-$, [P(C$_2$F$_4$H)(CF$_3$)$_2$F$_3$]$^-$, [P(C$_2$F$_3$H$_2$)$_3$F$_3$]$^-$, [P(C$_2$F$_5$)(CF$_3$)$_2$F$_3$]$^-$, [P(C$_6$F$_5$)$_3$F$_3$]$^-$, [P(C$_3$F$_7$)$_3$F$_3$]$^-$, [P(C$_2$F$_5$)$_2$F$_4$]$^-$, [(HO)$_2$P(O)O]$^-$, [(CH$_3$O)$_2$P(O)O]$^-$, [(C$_2$H$_5$O)$_2$P(O)O]$^-$, [(C$_2$F$_5$)$_2$P(O)O]$^-$, [(C$_2$F$_5$)P(O)O$_2$]$^{2-}$, [P(C$_6$F$_5$)$_2$F$_4$]$^-$, [(CH$_3$)$_2$P(O)O]$^-$, [CH$_3$P(O)O$_2$]$^{2-}$, [(CF$_3$)$_2$P(O)O]$^-$, [CF$_3$P(O)O$_2$]$^{2-}$, [BF$_4$]$^-$, [BF$_3$(CF$_3$)]$^-$, [BF$_2$(C$_2$F$_5$)$_2$]$^-$, [BF$_3$(C$_2$F$_5$)]$^-$, [BF$_2$(CF$_3$)$_2$]$^-$, [B(C$_2$F$_5$)$_4$]$^-$, [BF$_3$(CN)]$^-$, [BF$_2$(CN)$_2$]$^-$, [B(CN)$_4$]$^-$, [B(OCH$_3$)$_4$]$^-$, [B(CF$_3$)$_4$]$^-$, [B(OCH$_3$)$_2$(OC$_2$H$_5$)$_2$]$^-$, [B(O$_2$C$_2$H$_4$)$_2$]$^-$, [B(O$_2$C$_2$H$_2$)$_2$]$^-$, [B(O$_2$C$_6$H$_4$)$_2$]$^-$, [N(CN)$_2$]$^-$, [N(CF$_3$)$_2$]$^-$, [HSO$_4$]$^-$, [ClO$_4$]$^-$, [SiF$_6$]$^-$, [SCN]$^-$ or [NO$_3$]$^-$.

Very particular preference is given to compounds of the formula (4) in which the substituents R in each case, independently of one another, denote methyl, ethyl, n-propyl, isopropyl, n-butyl, tert-butyl, sec-butyl, n-hexyl, n-octyl, cyclohexyl or phenyl or two substituents R are bonded to one another in such a way that an imidazolidinium cation is formed and the counteranion A$^-$ denotes [CH$_3$OSO$_3$]$^-$, [CH$_3$SO$_3$]$^-$, [C$_8$H$_{17}$SO$_3$]$^-$, [CH$_3$C$_6$H$_4$SO$_3$]$^-$, [C$_2$F$_5$SO$_3$]$^-$, [(C$_2$F$_5$)$_3$PF$_3$]$^-$, [(C$_2$F$_5$)$_2$PF$_4$]$^-$, [(C$_4$F$_9$)$_3$PF$_3$]$^-$, [(C$_3$F$_7$)$_3$PF$_3$]$^-$, [(HO)$_2$P(O)O]$^-$, [(CH$_3$O)$_2$P(O)O]$^-$, [(C$_2$F$_5$)$_2$P(O)O]$^-$, [(C$_2$F$_5$)P(O)O$_2$]$^{2-}$, [B(CN)$_4$]$^-$, [B(CF$_3$)$_4$]$^-$, [B(C$_2$F$_5$)F$_3$]$^-$, [N(CN)$_2$]$^-$, [N(CF$_3$)$_2$]$^-$, [N(SO$_2$CF$_3$)$_2$]$^-$, [HSO$_4$]$^-$, [ClO$_4$]$^-$, [SCN]$^-$ or [NO$_3$]$^-$.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. on a Bruker Avance 250 spectrometer. The measurement frequencies of the various nuclei are: $^1$H: 250.13 MHz, $^{19}$F: 235.357 MHz and $^{31}$P: 101.254 MHz. The referencing method is indicated separately for each spectrum or each data set.

EXAMPLE 1

A) 1,3-Dimethyl-2-chloroimidazolidinium tris(pentafluoroethyl)trifluorophosphate

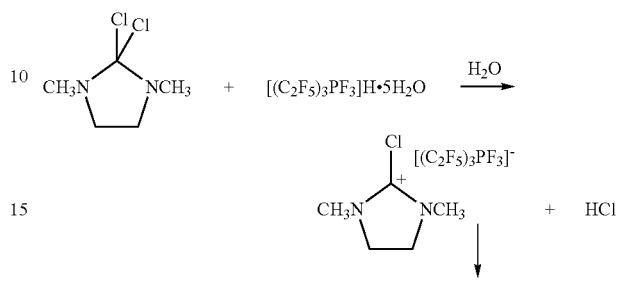

258.6 g (0.482 mol) of tris(pentafluoroethyl)trifluorophosphoric acid pentahydrate are added at room temperature with stirring to a solution of 80.0 g (0.473 mol) of 2,2-dichloro-1,3-dimethylimidazolidine in 300 ml of water. The mixture is stirred for half an hour, and the solid is subsequently filtered off. After repeated washing with 100 ml of water, the crystals formed are dried at 60° C. under a reduced pressure of 10.0 Pa, giving 1,3-dimethyl-2-chloroimidazolidinium tris(pentafluoroethyl)trifluorophosphate in a yield of 95.9%, based on dichloroimidazolidine.

m.p.: 151-152° C.

$^1$H NMR (reference: TMS internal; CD$_3$CN), ppm: 3.10 s (2CH$_3$), 3.90 s (2CH$_2$).

$^{19}$F NMR (reference, CCl$_3$F internal; CD$_3$CN), ppm: −43.57 d,m (PF), −79.62 m (CF$_3$), −81.31 m (2CF$_3$), −87.03 d,m (PF$_2$), −115.03 dm (CF$_2$) −115.62 dm (2CF$_2$); $^1$J$_{P,F}$=889 Hz, $^1$J$_{P,F}$=906 Hz, $^2$J$_{P,F}$=87 Hz, $^2$J$_{P,F}$=105 Hz.

$^{31}$P NMR (reference: 85% H$_3$PO$_4$ external; CD$_3$CN), ppm: −148.7 d,t,m.

B) 1,3-Dimethyl-2-diethylaminoimidazolidinium tris(pentafluoroethyl)-trifluorophosphate

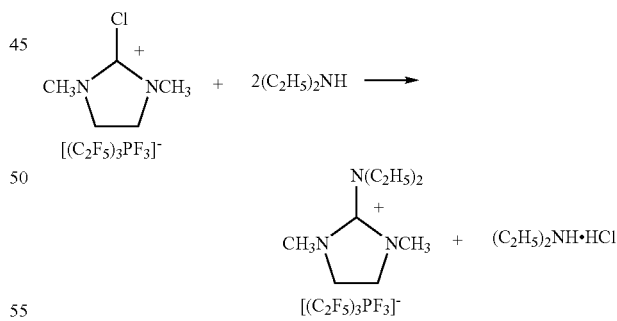

63.5 g (0.868 mol) of diethylamine are added over the course of 10 minutes at room temperature with stirring to 167.5 g (0.289 mol) of 1,3-dimethyl-2-chloroimidazolidinium tris(pentafluoroethyl)trifluorophosphate. The reaction mixture is stirred for 12 hours, and the excess diethylamine is subsequently distilled off. The liquid residue is washed a number of times with 100 ml of water and subsequently dried at 60° C. under reduced pressure (10.0 Pa), giving 169.2 g of 1,3-dimethyl-2-diethylaminoimidazolidinium tris(pentafluoroethyl)trifluorophosphate, corresponding to a yield of 95.2%.

¹H NMR (reference: TMS internal; CD₃CN), ppm: 1.15 t (2CH₃), 2.90 s (2CH₃), 3.30 q (2CH₂), 3.63 s (2CH₂), ³J$_{HH}$=7.1 Hz.

¹⁹F NMR (reference: CCl₃F internal; CD₃CN), ppm: −43.59 d,m (PF), −79.65 m (CF₃), −81.35 m (2CF₃), −87.03 d,m (PF₂), −115.05 dm (CF₂) −115.63 dm (2CF₂); ¹J$_{P,F}$=889 Hz, ¹J$_{P,F}$=899 Hz, ²J$_{P,F}$=87 Hz, ²J$_{P,F}$=105 Hz.

³¹P NMR (reference: 85% H₃PO₄ external; CD₃CN), ppm: −148.9 d,t,m.

C) 1,3-Dimethyl-2-dibutylaminoimidazolidinium tris(pentafluoroethyl)trifluorophosphate

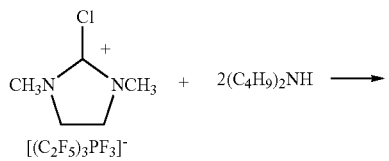

13.4 g (103.7 mmol) of dibutylamine are added over the course of 10 minutes at room temperature with stirring to 20.0 g (34.6 mmol) of 1,3-dimethyl-2-chloroimidazolidinium tris(pentafluoroethyl)trifluorophosphate. The reaction mixture is stirred for 12 hours at room temperature and for 2 hours at 60° C. The excess dibutylamine is removed by washing with hexane. The residue obtained is washed a number of times with 50 ml of water and subsequently dried at 60° C. under reduced pressure (10.0 Pa), giving 22.1 g of 1,3-dimethyl-2-dibutylaminoimidazolidinium tris(pentafluoroethyl)trifluorophosphate, corresponding to a yield of 95.1%.

m.p.: 36-38° C.

¹H NMR (reference: TMS internal; CD₃CN), ppm: 0.92 t (2CH₃), 1.30 m (2CH₂), 1.55 m (2CH₂), 2.91 s (2CH₃), 3.23 d,d (2CH₂), 3.64 s (2CH₂), ³J$_{HH}$=7.3 Hz.

¹⁹F NMR (reference: CCl₃F internal; CD₃CN), ppm: −43.64 d,m (PF), −79.68 m (CF₃), −81.37 m (2CF₃), −87.04 d,m (PF₂), −115.09 dm (CF₂) −115.62 dm (2CF₂); ¹J$_{P,F}$=890 Hz, ¹J$_{P,F}$=898 Hz, ²J$_{P,F}$=89 Hz, ²J$_{P,F}$=105 Hz.

³¹P NMR (reference: 85% H₃PO₄ external; CD₃CN), ppm: −149.0 d,t,m.

D) 1,3-Dimethyl-2-aminoimidazolidinium tris(pentafluoroethyl)trifluorophosphate

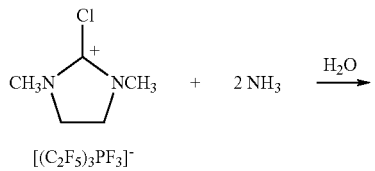

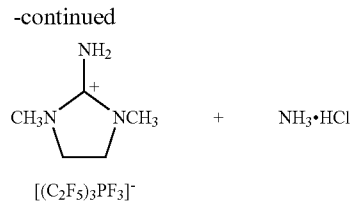

1.2 g (17.62 mmol) of a 25% aqueous solution of ammonia are added at room temperature with stirring to a solution of 2.0 g (3.46 mmol) of 1,3-dimethyl-2-chloroimidazolidinium tris(pentafluoroethyl)trifluorophospate in 5 ml of water. The mixture is stirred for 1 hour at room temperature and filtered. The precipitate is washed a number of times with 5 ml of water and dried under reduced pressure at 7 Pa and 50-60° C., giving 1.79 g of 1,3-dimethyl-2-aminoimidazolidinium tris(pentafluoroethyl)trifluorophosphate, corresponding to a yield of 92.5%.

m.p.: 67-68° C.

¹H NMR (reference: TMS internal; CD₃CN), ppm: 2.87 s (2CH₃), 3.57 s (2CH₂), 6.25 br.s (NH₂).

¹⁹F NMR (reference: CCl₃F internal; CD₃CN), ppm: −43.57 d,m (PF), −79.61 m (CF₃), −81.30 m (2CF₃), −87.03 d,m (PF₂), −115.07 dm (CF₂) −115.62 dm (2CF₂); ¹J$_{P,F}$=890 Hz, ¹J$_{P,F}$=900 Hz, ²J$_{P,F}$=86 Hz, ²J$_{P,F}$=105 Hz.

³¹P NMR (reference: 85% H₃PO₄ external; CD₃CN), ppm: −148.9 d,t,m.

E) 1,3-Dimethyl-2-diethylaminoimidazolidinium tris(pentafluoroethyl)- trifluorophosphate

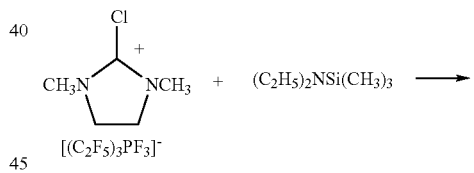

0.30 g (2.06 mmol) of N,N-diethyltrimethylsilylamine is added over the course of a few minutes at room temperature with stirring to 1.0 g (1.73 mmol) of 1,3-dimethyl-2-chloroimidazolidinium tris(pentafluoroethyl)trifluorophosphate in 15 ml of chloroform. The reaction mixture is stirred for 30 minutes at room temperature and for 30 minutes at 40-50° C. The volatile constituents are distilled off, and the residue obtained is dried at 50° C. under reduced pressure (7.0 Pa), giving 0.99 g of 1,3-dimethyl-2-diethyl-aminoimidazolidinium tris(pentafluoroethyl)trifluorophosphate, corresponding to a yield of 93.0%.

m.p.: 34-35° C.

The NMR spectra are identical to those from Example 1 B.

EXAMPLE 2

A) Bis(dimethylamino)chlorocarbenium tris(pentafluoroethyl)trifluorophosphate

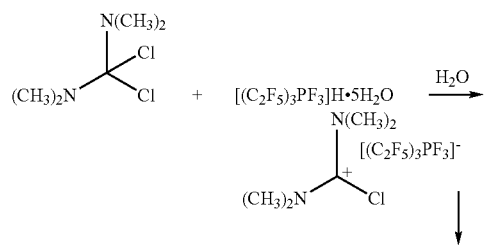

63.9 g (0.119 mol) of tris(pentafluoroethyl)trifluorophosphoric acid pentahydrate are added at room temperature with stirring to a solution of 20.0 g (0.117 mol) of bis(dimethylamino)dichloromethane in 100 ml of water. The mixture is stirred for half an hour, and the solid is subsequently filtered off. After repeated washing with 50 ml of water, the crystals formed are dried at 60° C. under a reduced pressure of 10.0 Pa, giving 63.4 g of bis(dimethyl-amino)chlorocarbenium tris(pentafluoroethyl)trifluorophosphate, corresponding to a yield of 93.3%.

m.p.: 102-103° C.

$^1$H NMR (reference: TMS internal; CD$_3$CN), ppm: 3.24 s (4CH$_3$).

$^{19}$F NMR (reference: CCl$_3$F internal; CD$_3$CN), ppm: −43.57 d,m (PF), −79.62 m (CF$_3$), −81.31 m (2CF$_3$), −87.01 d,m (PF$_2$), −115.06 dm (CF$_2$) −115.60 dm (2CF$_2$); $^1J_{P,F}$=889 Hz, $^1J_{P,F}$=901 Hz, $^2J_{P,F}$=85 Hz, $^2J_{P,F}$=108 Hz.

$^{31}$P NMR (reference: 85% H$_3$PO$_4$ external; CD$_3$CN), ppm: −149.0 d,t,m.

B) N,N,N',N'-tetramethyl-N'',N''-diethylguanidinium tris(pentafluoroethyl)trifluorophosphate

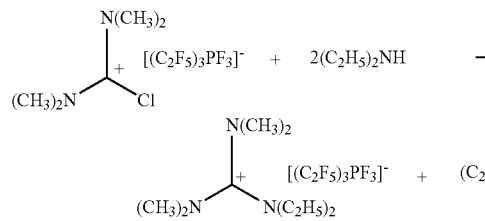

4.53 g (61.9 mmol) of diethylamine are added over the course of 5 minutes at room temperature with stirring to 12.0 g (20.7 mmol) of bis(dimethylamino)chlorocarbenium tris(pentafluoroethyl)trifluorophosphate. The reaction mixture is stirred for 12 hours, and the excess diethylamine is subsequently distilled off. The liquid residue is washed a number of times with 30 ml of water and subsequently dried at 60° C. under reduced pressure (10.0 Pa), giving 12.1 g of N,N,N',N'-tetramethyl-N'',N''-diethylguanidinium tris(pentafluoroethyl)trifluorophosphate, corresponding to a yield of 94.7%.

m.p.: 28-30° C.

$^1$H NMR (reference: TMS internal; CD$_3$CN), ppm: 1.12 t (2CH$_3$), 2.85 s (2CH$_3$), 2.87 s (2CH$_3$), 3.20 m (2CH$_2$), $^3J_{H,H}$=7.1 Hz.

$^{19}$F NMR (reference: CCl$_3$F internal; CD$_3$CN), ppm: −43.57 d,m (PF), −79.63 m (CF$_3$), −81.32 m (2CF$_3$), −87.0 d,m (PF$_2$), −115.01 dm (CF$_2$) −115.62 dm (2CF$_2$); $^1J_{P,F}$=889 Hz, $^1J_{P,F}$=901 Hz, $^2J_{P,F}$=85 Hz, $^2J_{P,F}$=105 Hz.

$^{31}$P NMR (reference: 85% H$_3$PO$_4$ external; CD$_3$CN), ppm: −148.9 d,t,m.

C) N,N,N',N'-tetramethyl-N'',N''-dibutylguanidinium tris(pentafluoroethyl)trifluorophosphate

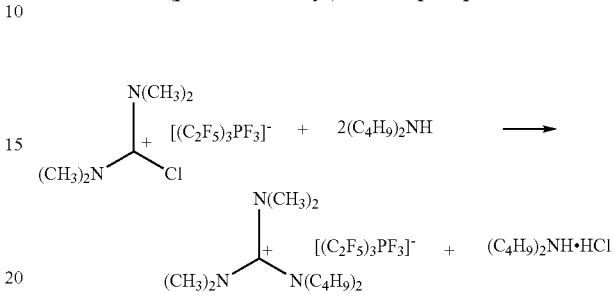

13.4 g (103.7 mmol) of dibutylamine are added over the course of 10 minutes at room temperature with stirring to 20.0 g (34.4 mmol) of bis(dimethylamino)chlorocarbenium tris(pentafluoroethyl)trifluorophosphate. The reaction mixture is stirred for 12 hours at room temperature and for 2 hours at 60° C. The excess dibutylamine is removed by washing with hexane. The liquid residue is washed a number of times with 50 ml of water and subsequently dried at 60° C. under reduced pressure (10.0 Pa), giving 22.6 g of N,N,N',N'-tetramethyl-N'',N''-dibutylguanidinium tris(pentafluoroethyl)trifluorophosphate, corresponding to a yield of 97.5%.

$^1$H NMR (reference: TMS internal; CD$_3$CN), ppm: 0.90 t (2CH$_3$), 1.20-1.70 m (4CH$_2$), 2.87 s (2CH$_3$), 2.88 s (2CH$_3$), 3.12 m (2CH$_2$), $^3J_{H,H}$=7.3 Hz.

$^{19}$F NMR (reference: CCl$_3$F internal; CD$_3$CN), ppm: −43.62 d,m (PF), −79.67 m (CF$_3$), −81.36 m (2CF$_3$), −87.01 d,m (PF$_2$), −115.09 dm (CF$_2$) −115.62 dm (2CF$_2$); $^1J_{P,F}$=889 Hz, $^1J_{P,F}$=898 Hz, $^2J_{P,F}$=85 Hz, $^2J_{P,F}$=105 Hz.

$^{31}$P NMR (reference: 85% H$_3$PO$_4$ external; CD$_3$CN), ppm: −148.9 d,t,m.

D) N,N,N',N'-tetramethyl-N'',N''-dicyclohexylguanidinium tris(pentafluoroethyl)trifluorophosphate

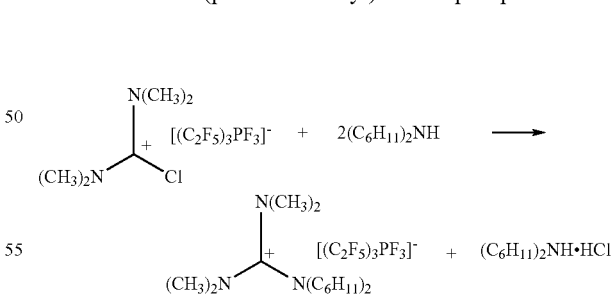

18.7 g (103.1 mmol) of dicyclohexylamine are added over the course of 10 minutes at room temperature with stirring to 20.0 g (34.4 mmol) of bis(dimethylamino)chlorocarbenium tris(pentafluoroethyl)trifluorophosphate. The reaction mixture is stirred for 12 hours at room temperature and for 2 hours at 60° C. The excess dicyclohexylamine is removed by washing with hexane. The residue obtained is washed a number of times with 50 ml of water and subsequently dried at 60° C. under reduced pressure (10.0 Pa), giving 22.8 g of N,N,N', N'-tetramethyl-N'',N''-dicyclohexylguanidinium tris(pentafluoroethyl)trifluorophosphate, corresponding to a yield of 91.3%.

m.p.: 68-70° C.

$^1$H NMR (reference: TMS internal; CD$_3$CN), ppm: 1.20-2.10 m (10 CH$_2$), 3.24 s (4CH$_3$), 6.26 t (2CH), $J_{H,H}$=45.5 Hz.

$^{19}$F NMR (reference: CCl$_3$F internal; CD$_3$CN), ppm: -43.64 d,m (PF), -79.70 m (CF$_3$), -81.40 m (2CF$_3$), -87.05 d,m (PF$_2$), -115.13 dm (CF$_2$) -115.69 dm (2CF$_2$); $^1J_{P,F}$=889 Hz, $^1J_{P,F}$=898 Hz, $^2J_{P,F}$=87 Hz, $^2J_{P,F}$=107 Hz.

$^{31}$P NMR (reference: 85% H$_3$PO$_4$ external; CD$_3$CN), ppm: -148.9 d,t,m.

EXAMPLE 3

A) Bis(dimethylamino)chlorocarbenium bis(trifluoromethanesulfonyl)imide

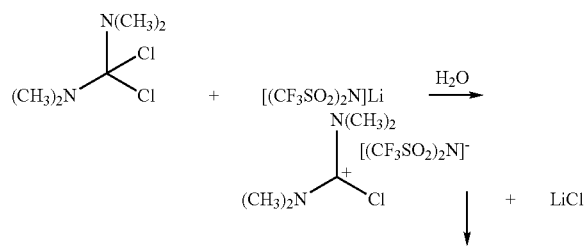

134.1 g (0.467 mol) of lithium bis(trifluoromethanesulfonyl)imide in 200 ml of water are added with stirring at room temperature to a solution of 80.0 g (0.468 mol) of bis(dimethylamino)dichloromethane in 300 ml of water. The mixture is stirred for half an hour, and the solid is subsequently filtered off. After repeated washing with 100 ml of water, the crystals formed are dried at 50° C. under a reduced pressure of 10.0 Pa, giving 165.5 g of bis(dimethylamino)chlorocarbenium bis(trifluoromethanesulfonyl)imide, corresponding to a yield of 85.1%.

m.p.: 68-70° C.

$^1$H NMR (reference: TMS internal; CD$_3$CN), ppm: 3.24 s (4CH$_3$).

$^{19}$F NMR (reference: CCl$_3$F internal; CD$_3$CN), ppm: -78.87 s (2CF$_3$).

B) Bis(dimethylamino)chlorocarbenium bis(trifluoromethanesulfonyl)imide

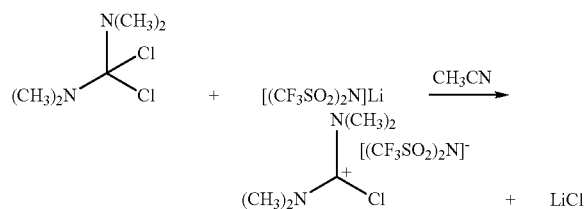

0.84 g (2.92 mmol) of lithium bis(trifluoromethanesulfonyl)imide in 4 ml of acetonitrile are added with stirring at room temperature to a solution of 0.5 g (2.92 mmol) of bis(dimethylamino)dichloromethane in 4 ml of acetonitrile. The mixture is stirred for 12 hours, and the solid LiCl is subsequently filtered off. Acetonitrile is distilled off. The crystals formed are dried at 50° C. under a reduced pressure of 10.0 Pa, giving 1.2 g of bis(dimethylamino)chlorocarbenium bis(trifluoromethanesulfonyl)imide, corresponding to a yield of 98.8%.

The compound exhibits identical NMR spectra as prepared under 3.A).

C) N,N,N',N'-tetramethyl-N'',N''-dibutylguanidinium bis(trifluoromethanesulfonyl)imide

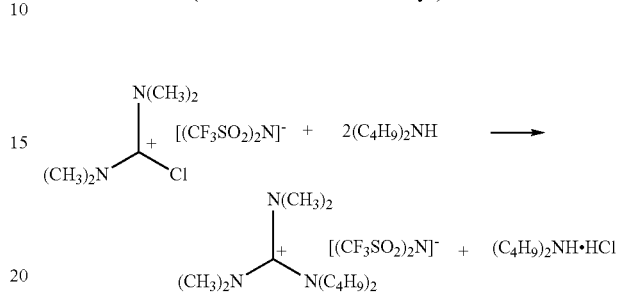

141.3 g (1.1 mol) of dibutylamine are added over the course of 20 minutes at room temperature with stirring to 151.4 g (0.364 mol) of bis(dimethylamino)chlorocarbenium bis(trifluoromethanesulfonyl)imide. The reaction mixture is stirred for 12 hours at room temperature and for 2 hours at 60° C. The excess dibutylamine is removed by washing with hexane. The liquid residue is washed a number of times with 100 ml of water and subsequently dried at 60° C. under reduced pressure (10.0 Pa), giving 183.1 g of N,N,N',N'-tetramethyl-N'',N''-dibutylguanidinium bis(trifluoromethanesulfonyl)imide, corresponding to a yield of 98.9%;

$^1$H NMR (reference: TMS internal; CD$_3$CN), ppm: 0.90 t (2CH$_3$), 1.20-1.70 m (4CH$_2$), 2.87 s (2CH$_3$), 2.88 s (2CH$_3$), 3.12 m (2CH$_2$), $^3J_{H,H}$=7.3 Hz.

$^{19}$F NMR (reference: CCl$_3$F internal; CD$_3$CN), ppm: -78.97 s (2CF$_3$).

EXAMPLE 4

A) Bis(dimethylamino)chlorocarbenium trifluoromethanesulfonate

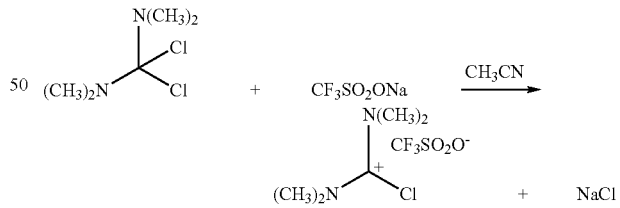

2.01 g (11.7 mmol) of sodium trifluoromethanesulfonate in 20 ml of acetonitrile are added with stirring at room temperature to a solution of 2.0 g (11.7 mmol) of bis(dimethylamino)dichloromethane in 20 ml of acetonitrile. The mixture is stirred for one hour, and 40 ml of diethyl ether are added. After stirring for 12 hours, the solid NaCl is subsequently filtered off. The solvent is distilled off, and the crystals formed are dried under a reduced pressure of 10.0 Pa, giving 3.29 g of bis(dimethylamino)chlorocarbenium trifluoromethanesulfonate, corresponding to a yield of 98.8%.

m.p.: 93-96° C.

$^1$H NMR (reference: TMS internal; CD$_3$CN), ppm: 3.24 s (4CH$_3$).

$^{19}$F NMR (reference: CCl$_3$F internal; CD$_3$CN), ppm: −77.91 s (CF$_3$).

B) Bis(dimethylamino)chlorocarbenium trifluoromethanesulfonate

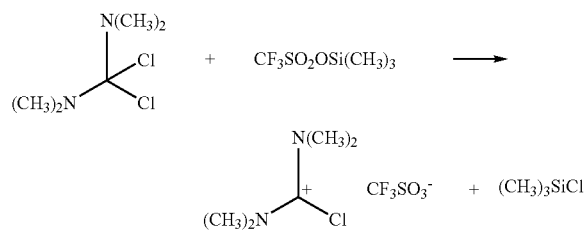

0.5 g (2.92 mmol) of bis(dimethylamino)dichloromethane are added at room temperature to 0.86 g (3.87 mmol) of trimethylsilyl trifluoromethanesulfonate, prepared by reaction of 0.42 g of trimethylchlorosilane with 0.58 g of trifluoromethanesulfonic acid at room temperature. The reaction mixture is stirred for 5 minutes, and all volatile products are subsequently removed under reduced pressure. The residue is dried under reduced pressure at 7 Pa and 50° C., giving 0.82 g of bis(dimethylamino)chlorocarbenium trifluoromethanesulfonate, corresponding to a yield of 98.7%.

m.p.: 175-177° C.

The NMR spectra are identical to those of Example 4.A).

C) Hexamethylguanidinium trifluoromethanesulfonate

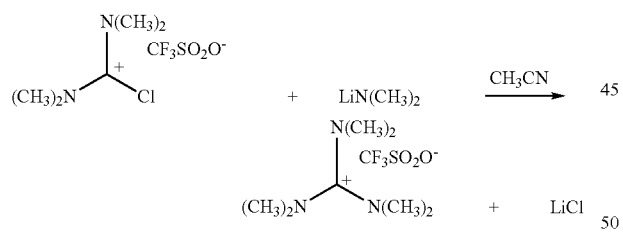

0.225 g (4.41 mmol) of lithium dimethylamide are added at room temperature to 1.26 g (4.42 mmol) of bis(dimethylamino)chlorocarbenium trifluoromethanesulfonate in 20 ml of acetonitrile. The reaction mixture is stirred for 12 hours, and LiCl is subsequently filtered off. The solvent is distilled off, and the residue is washed with 20 ml of diethyl ether and subsequently dried under reduced pressure (8.0 Pa), giving 1.25 g of hexamethylguanidinium trifluoromethanesulfonate, corresponding to a yield of 96.7%.

$^1$H NMR (reference: TMS internal; CD$_3$CN), ppm: 2.89 s (6CH$_3$).

$^{19}$F NMR (reference: CCl$_3$F internal; CD$_3$CN), ppm: −77.90 s (CF$_3$).

EXAMPLE 5

A) 1,3-Dimethyl-2-chloroimidazolidinium trifluoromethanesulfonate

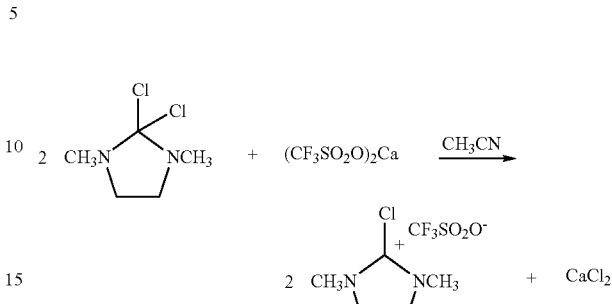

5.0 g (14.8 mmol) of calcium trifluoromethanesulfonate are added with stirring at room temperature to a solution of 5.0 g (29.6 mmol) of 2,2-dichloro-1,3-dimethylimidazolidine in 80 ml of acetonitrile. The mixture is stirred for 12 hours, and the solid CaCl$_2$ is subsequently filtered off. Acetonitrile is distilled off, and the residue is washed with 40 ml of diethyl ether. The crystals formed are dried under a reduced pressure of 10.0 Pa, giving 8.28 g of 1,3-dimethyl-2-chloroimidazolidinium trifluoromethanesulfonate, corresponding to a yield of 98.9%.

m.p.: 62-63° C.

$^1$H NMR (reference: TMS internal; CD$_3$CN), ppm: 3.10 s (2CH$_3$), 3.90 s (2CH$_2$).

$^{19}$F NMR (reference: CCl$_3$F internal; CD$_3$CN), ppm: −77.88 s (CF$_3$).

B) 1,3-Dimethyl-2-diethylaminoimidazolidinium trifluoromethanesulfonate

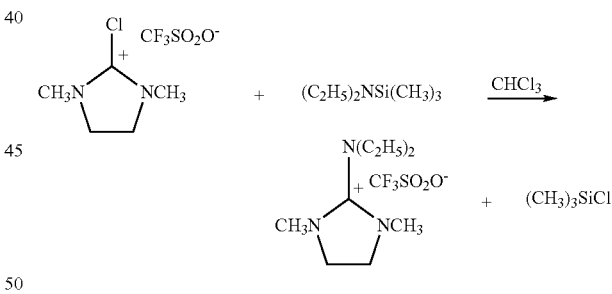

0.62 g (4.27 mmol) of N,N-diethyltrimethylsilylamine are added over the course of a few minutes at room temperature with stirring to 1.0 g (3.54 mmol) of 1,3-dimethyl-2-chloroimidazolidinium trifluoromethanesulfonate in 15 ml of chloroform. The reaction mixture is stirred for 30 minutes at room temperature and for 30 minutes at 40-50° C. The volatile constituents are distilled off, and the residue obtained is dried at 50° C. under reduced pressure (7.0 Pa), giving 1.11 g of 1,3-dimethyl-2-diethylaminoimidazolidinium trifluoromethanesulfonate as an oil, corresponding to a yield of 98.2%.

$^1$H NMR (reference: TMS internal; CD$_3$CN), ppm: 1.17 t (2CH$_3$), 2.92 s (2CH$_3$), 3.32 q (2CH$_2$), 3.65 s (2CH$_2$), $^3J_{H,H}$=7.1 Hz.

$^{19}$F NMR (reference: CCl$_3$F internal; CD$_3$CN), ppm: −78.02 s (CF$_3$).

EXAMPLE 6

N,N,N',N'-tetramethyl-N''-ethylguanidinium tris(pentafluoroethyl)trifluorophosphate

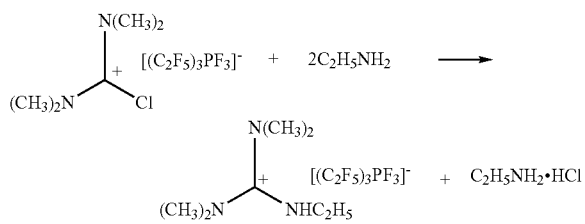

24.0 g of an aqueous solution (70%) of ethylamine are added with stirring and ice-cooling to 43.20 g (74.4 mmol) of bis(dimethylamino)chlorocarbenium tris(pentafluoroethyl)trifluorophosphate, prepared analogously to Example 2.A). The reaction mixture is subsequently stirred for 3 hours at room temperature. The mixture is washed with 50 ml of water and subsequently dried at 60° C. under reduced pressure (7.0 Pa), giving 42.1 g of the liquid N,N,N',N'-tetramethyl-N''-ethylguanidinium tris(pentafluoroethyl)trifluorophosphate, corresponding to a yield of 96.0%.

$^1$H NMR (reference: TMS internal; $CD_3CN$), ppm: 1.21 t ($CH_3$), 2.21 s (4$CH_3$), 3.21 d,q ($CH_2$), 5.80 br.s (NH), $^3J_{H,H}$=7.2 Hz, $^3J_{H,H}$=5.6 Hz.

$^{19}$F NMR (reference: $CCl_3F$ internal; $CD_3CN$), ppm: −43.57 d,m (PF), −79.66 m ($CF_3$), −81.36 m (2$CF_3$), −86.97 d,m ($PF_2$), −115.05 dm ($CF_2$) −115.60 dm (2$CF_2$); $^1J_{P,F}$=889 Hz, $^1J_{P,F}$=901 Hz, $^2J_{P,F}$=83 Hz, $^2J_{P,F}$=105 Hz.

$^{31}$P NMR (reference: 85% $H_3PO_4$ external; $CD_3CN$), ppm: −148.9 d,t,m.

EXAMPLE 7

1,3-Dimethyl-2-ethylaminoimidazolidinium tris(pentafluoroethyl)trifluorophosphate

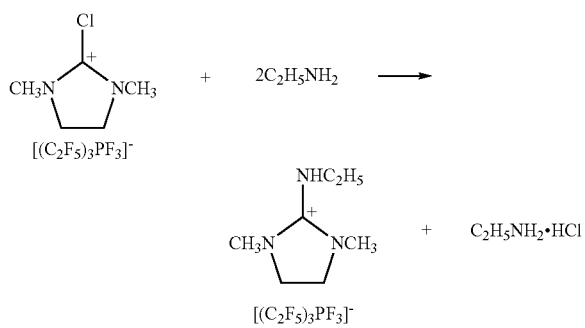

2.31 g of an aqueous solution (70%) of ethylamine are added with stirring and ice-cooling to 4.07 g (7.03 mmol) of 1,3-dimethyl-2-chloroimidazolidinium tris(pentafluoroethyl)trifluorophosphate, prepared analogously to Example 1.A). The reaction mixture is subsequently stirred for 3 hours at room temperature. The mixture is subsequently dried at 60° C. under reduced pressure (7.0 Pa), giving 3.76 g of the liquid 1,3-dimethyl-2-ethylaminoimidazolidinium tris(pentafluoroethyl)trifluorophosphate, corresponding to a yield of 91.1%.

$^1$H NMR (reference: TMS internal; $CD_3CN$), ppm: 1.25 t ($CH_3$), 2.96 s (2$CH_3$), 3.45 q ($CH_2$), 3.59 s (2$CH_2$), $^3J_{H,H}$=7.3 Hz.

$^{19}$F NMR (reference: $CCl_3F$ internal; $CD_3CN$), ppm: −43.63 d,m (PF), −79.73 m ($CF_3$), −81.42 m (2$CF_3$), −87.07 d,m ($PF_2$), −115.07 dm ($CF_2$) −115.67 dm (2$CF_2$); $^1J_{P,F}$=890 Hz, $^1J_{P,F}$=901 Hz, $^2J_{P,F}$=85 Hz, $^2J_{P,F}$=105 Hz.

$^{31}$P NMR (reference: 85% $H_3PO_4$ external; $CD_3CN$), ppm: −148.9 d,t,m.

EXAMPLE 8

A) Bis(dimethylamino)chlorocarbenium perchlorate

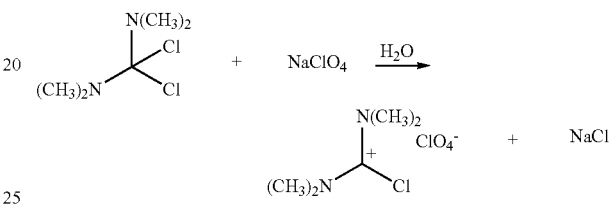

3.60 g of sodium perchlorate in 10 ml of water are added with stirring to a solution of 5.00 g (29.2 mmol) of bis(dimethylamino)dichloromethane in 20 ml of water. The reaction mixture is subsequently stirred for 1 hour with ice-cooling. The residue is filtered off and washed with 10 ml of ice-water and subsequently dried at 50° C. under reduced pressure (7.0 Pa), giving 6.64 g of bis(dimethylamino)chlorocarbenium perchlorate, corresponding to a yield of 94.0%.

m.p.: 97-99° C.

$^1$H NMR (reference: TMS internal; $CD_3CN$), ppm: 3.27 s (4$CH_3$).

B) N,N,N',N'-tetramethyl-N'',N''-diethylguanidinium perchlorate

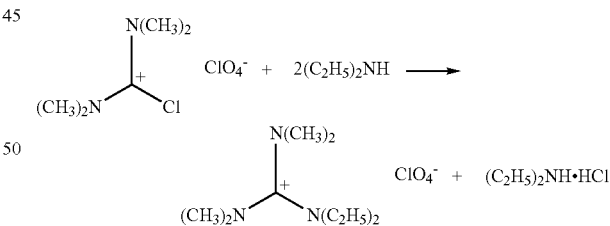

3.42 g (46.8 mmol) of diethylamine are added with stirring and ice-cooling to 5.00 g (21.3 mmol) of bis(dimethylamino)chlorocarbenium perchlorate. The reaction mixture is subsequently stirred for 1 hour at room temperature and subsequently added to 20 ml of water. The organic phase is separated off and washed with 20 ml of water. The liquid is subsequently dried at 50° C. under reduced pressure (7.0 Pa), giving 5.17 g of N,N,N',N'-tetramethyl-N'',N''-diethylguanidinium perchlorate, corresponding to a yield of 89.6%.

$^1$H NMR (reference: TMS internal; $CD_3CN$), ppm: 1.15 t (2$CH_3$), 2.88 s (2$CH_3$), 2.91 S (2$CH_3$), 3.23 m (2$CH_2$), $^3J_{H,H}$=7.2 Hz.

EXAMPLE 9

A) Bis(dimethylamino)chlorocarbenium tosylate

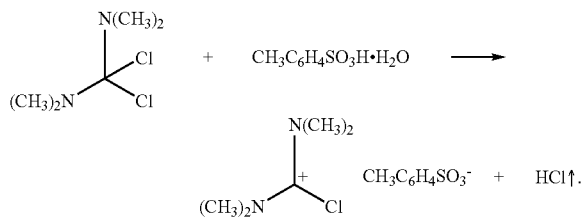

3.0 g (17.5 mmol) of bis(dimethylamino)dichloromethane and 3.33 g (17.5 mmol) of p-toluenesulfonic acid monohydrate are mixed. The mixture is heated to 100° C. over the course of 30 min, and a vacuum of 7 Pa is subsequently applied over one hour. Cooling to room temperature gives 5.25 g of bis(dimethylamino)chlorocarbenium tosylate, corresponding to a yield of 97.8%.

m.p.: 122-126° C.

$^1$H NMR (reference: TMS internal; CD$_3$CN), ppm: 2.33 s (CH$_3$), 3.24 s (4CH$_3$), 7.15, 7.18 (A,B; 2H), 7.58, 7.62 (A,B; 2H).

B) Hexamethylguanidinium tosylate

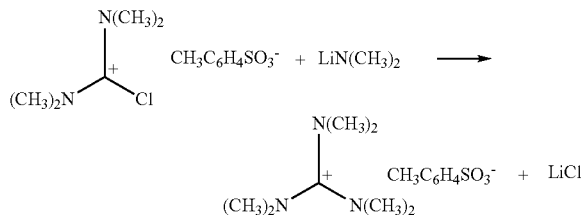

1.50 g (4.89 mmol) of bis(dimethylamino)chlorocarbenium tosylate and 0.25 g (4.90 mmol) of lithium dimethylamide are dissolved in 15 ml of acetonitrile under a protective-gas atmosphere (argon). The reaction mixture is stirred for 5 hours at room temperature, and LiCl is subsequently filtered off. The salt LiCl is washed with 5 ml of acetonitrile, and the organic phases are combined. The solvent is distilled off, and the residue is dried under reduced pressure at 7 Pa and 50° C., giving 1.49 g of hexamethylguanidinium tosylate, corresponding to a yield of 96.6%.

m.p.: 103-104° C.

$^1$H NMR (reference: TMS internal; CD$_3$CN), ppm: 2.33 s (CH$_3$), 2.86 s (6CH$_3$), 7.13, 7.16 (A,B; 2H), 7.57, 7.61 (A,B; 2H).

EXAMPLE 10

A) Bis(dimethylamino)chlorocarbenium hydrogensulfate

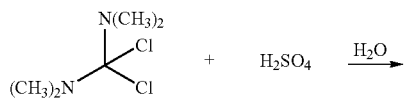

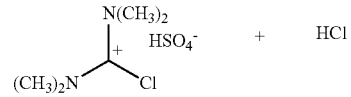

3.24 g (33 mmol) of sulfuric acid are added with stirring and ice-cooling to a solution of 5.65 g (33.0 mmol) of bis(dimethylamino)dichloromethane in 30 ml of water. The reaction mixture is warmed to room temperature. All volatile compounds are removed under reduced pressure (7.0 Pa), giving 7.68 g of highly viscous bis(dimethylamino)chlorocarbenium hydrogensulfate, corresponding to a virtually quantitative yield.

$^1$H NMR (reference: TMS internal; D$_2$O), ppm: 3.05 s (4CH$_3$).

B) N,N,N',N'-tetramethyl-N'',N''-diethylguanidinium hydrogensulfate

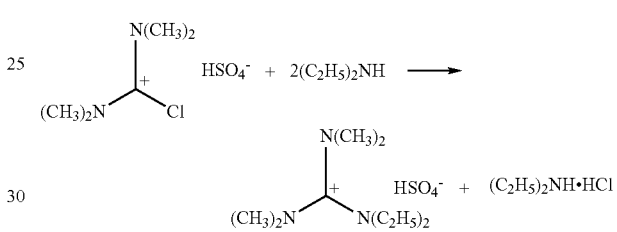

4.20 g (57.4 mmol) of diethylamine are added with stirring and ice-cooling to 6.00 g (25.8 mmol) of bis(dimethylamino)chlorocarbenium hydrogensulfate. The reaction mixture is subsequently stirred for 1 hour at room temperature, and 50 ml of water are subsequently added. The organic phase is separated off, and the aqueous phase is extracted with 50 ml of dichloromethane. The combined organic phases are washed with 20 ml of water, and the solvent is distilled off under reduced pressure. The residue is subsequently dried at 50° C. under reduced pressure (7.0 Pa), giving 5.7 g of viscous N,N,N',N'-tetramethyl-N'',N''-diethylguanidinium hydrogensulfate, corresponding to a yield of 82.0%.

$^1$H NMR (reference: TMS internal; D$_2$O), ppm: 0.99 t (2CH$_3$), 2.77 s (4CH$_3$), 3.13 m (2CH$_2$), $^3$J$_{H,H}$=7.2 Hz.

EXAMPLE 11

A) 1,3-Dimethyl-2-chloroimidazolidinium nitrate

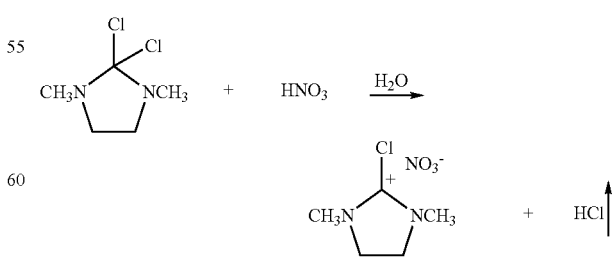

2.34 g (24.1 mmol) of a 65% nitric acid are added with vigorous stirring to 3.77 g (22.3 mmol) of 2,2-dichloro-1,3-dimethylimidazolidine. This reaction mixture is evacuated firstly at room temperature for one hour at 4 kPa and for 20 min at 7 Pa. After cooling using an ice bath, the mixture is evacuated again for 6 hours at 7 Pa, giving 3.7 g of 1,3-dimethyl-2-chloroimidazolidinium nitrate as an oil, corresponding to a yield of 85.1%.

$^1$H NMR (reference: TMS internal; D$_2$O), ppm: 3.05 s (2CH$_3$), 3.89 s (2CH$_2$).

B) 1,3-Dimethyl-2-dimethylaminoimidazolidinium nitrate

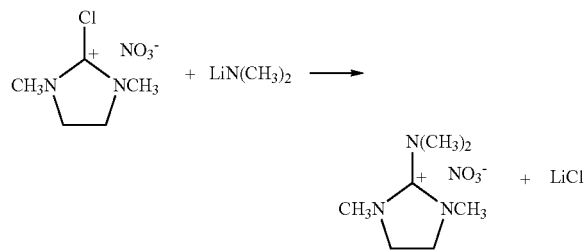

3.00 g (15.34 mmol) of 1,3-dimethyl-2-chloroimidazolidinium nitrate and 0.78 g (15.29 mmol) of lithium dimethylamide are dissolved in 20 ml of acetonitrile under a protective-gas atmosphere (argon). The reaction mixture is stirred for 5 hours at room temperature, and LiCl is subsequently filtered off. The salt LiCl is washed with 5 ml of acetonitrile, and the organic phases are combined. The solvent is distilled off, and the residue is dried under reduced pressure at 7 Pa and 50° C., giving 2.91 g of 1,3-dimethyl-2-dimethylaminoimidazolidinium nitrate as a liquid, corresponding to a yield of 92.2%.

$^1$H NMR (reference: TMS internal; CD$_3$CN), ppm: 2.96 s (2CH$_3$), 2.99 s (2CH$_3$), 3.63 s (2CH$_2$).

EXAMPLE 12

A) Bis(dimethylamino)chlorocarbenium trifluoroacetate

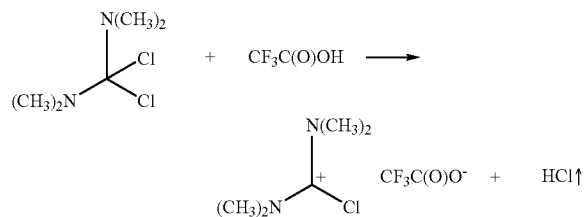

2.1 g (18.4 mmol) of trifluoroacetic acid are added with stirring to 3.0 g (17.5 mmol) of bis(dimethylamino)dichloromethane. The reaction is stirred for one hour at room temperature, and all volatile products are subsequently removed under reduced pressure at 7 Pa and 60° C., giving 4.19 g of bis(dimethylamino)chlorocarbenium trifluoroacetate as a very viscous oil, corresponding to a yield of 96.1%.

$^1$H NMR (reference: TMS internal; CD$_3$CN), ppm: 3.27 s (4CH$_3$).

$^{19}$F NMR (reference: CCl$_3$F internal; CD$_3$CN), ppm: −75.63 s (CF$_3$).

B) Hexamethylguanidinium trifluoroacetate

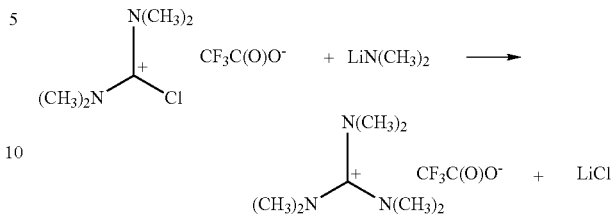

1.85 g (7.44 mmol) of bis(dimethylamino)chlorocarbenium trifluoroacetate and 0.38 g (7.45 mmol) of lithium dimethylamide are dissolved in 15 ml of acetonitrile under a protective-gas atmosphere (argon). The reaction mixture is stirred for 5 hours at room temperature, and LiCl is subsequently filtered off. The salt LiCl is washed with 5 ml of acetonitrile, and the organic phases are combined. The solvent is distilled off, and the residue is dried under reduced pressure at 7 Pa and 50° C., giving 1.81 g of hexamethylguanidinium trifluoroacetate as a viscous oil, corresponding to a yield of 99.2%.

$^1$H NMR (reference: TMS internal; CD$_3$CN), ppm: 2.89 s (6CH$_3$).

$^{19}$F NMR (reference: CCl$_3$F internal; CD$_3$CN), ppm: −75.56 s (CF$_3$).

EXAMPLE 13

A) Bis(dimethylamino)chlorocarbenium thiocyanate

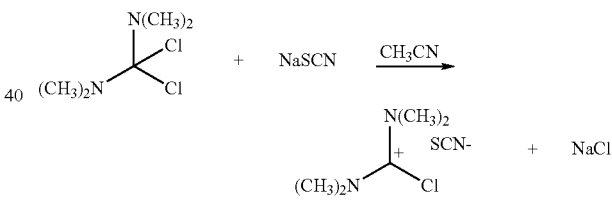

2.84 g (35.0 mmol) of sodium thiocyanate are added at room temperature to a solution of 3.0 g (17.5 mmol) of bis(dimethylamino)dichloromethane in 50 ml of acetonitrile. The reaction mixture is stirred for 24 hours, and the precipitate NaCl is subsequently filtered off. The solvent is subsequently distilled off, and the residue is extracted a number of times with 50 ml of dichloromethane. After distillation of the dichloromethane, the residue is dried at 60° C. and 7 Pa, giving 2.99 g of the liquid bis(dimethylamino)chlorocarbenium thiocyanate, corresponding to a yield of 88.2%.

$^1$H NMR (reference: TMS internal; CD$_3$CN), ppm: 3.27 s (4CH$_3$).

B) Hexamethylguanidinium thiocyanate

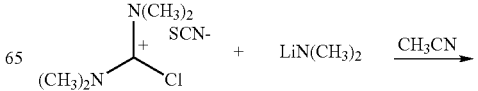

-continued

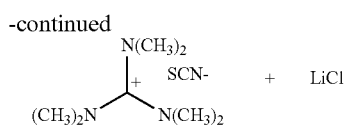

1.00 g (5.16 mmol) of bis(dimethylamino)chlorocarbenium thiocyanate and 0.26 g (5.10 mmol) of lithium dimethylamide are dissolved in 10 ml of acetonitrile under a protective-gas atmosphere (argon). The reaction mixture is stirred for 5 hours at room temperature, and LiCl is subsequently filtered off. The salt LiCl is washed with 2 ml of acetonitrile, and the organic phases are combined. The solvent is distilled off, and the residue is dried under reduced pressure at 7 Pa and 50° C., giving 0.99 g of hexamethylguanidinium thiocyanate as an oil, corresponding to a yield of 94.8%.

$^1$H NMR (reference: TMS internal; CD$_3$CN), ppm: 2.89 s (6CH$_3$).

EXAMPLE 14

A) Bis(dimethylamino)chlorocarbenium tetracyanoborate

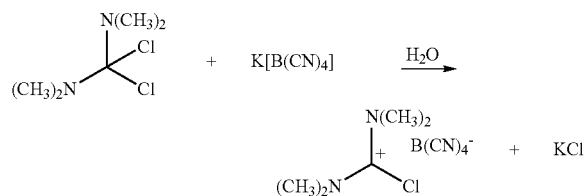

13.4 g (78.3 mmol) of bis(dimethylamino)dichloromethane are added at room temperature with stirring to a solution of 12.0 g (77.9 mmol) of potassium tetracyanoborate in 200 ml of water. The reaction mixture is stirred for 10 minutes and cooled with the aid of an ice bath. The precipitate is subsequently filtered off and washed a number of times with 30 ml of ice-water. The combined filtrates were dried for 3 hours under reduced pressure at 7 Pa and 60° C. in an oil bath, giving 13.4 g of bis(dimethylamino)chlorocarbenium tetracyanoborate as an oil, corresponding to a yield of 68.7%.

$^1$H NMR (reference: TMS internal; CD$_3$CN), ppm: 3.27 s (4CH$_3$).

$^{11}$B NMR (reference: BF$_3$.Et$_2$O external; CD$_3$CN), ppm: −38.59 s.

B) N,N,N',N'-tetramethyl-N'',N''-diethylguanidinium tetracyanoborate

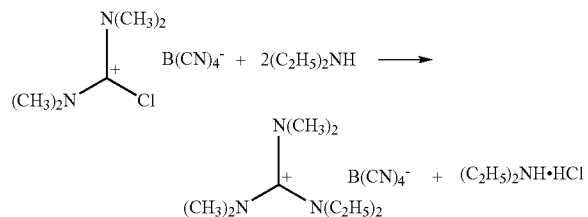

10.5 g (143.6 mmol) of diethylamine are added with stirring and cooling to 12.0 g (47.9 mmol) of bis(dimethylamino) chlorocarbenium tetracyanoborate. The reaction mixture is stirred for 3 hours at room temperature, and 30 ml of water are then added. The lower phase is separated off and diluted with 30 ml of dichloromethane. The organic phases are subsequently washed a number of times with 30 ml of water and dried using MgSO$_4$. The solvent is then distilled off, and the residue is dried for 3 hours under reduced pressure at 7 Pa and 60° C., giving 13.4 g of N,N,N',N'-tetramethyl-N'',N''-diethylguanidinium tetracyanoborate as a liquid, corresponding to a yield of 97.4%.

$^1$H NMR (reference: TMS internal; CD$_3$CN), ppm: 1.15 t (2CH$_3$), 2.88 s (2CH$_3$), 2.90 s (2CH$_3$), 3.23 m (2CH$_2$), $^3J_{H,H}$=7.2 Hz.

$^{11}$B NMR (reference: BF$_3$.Et$_2$O external; CD$_3$CN), ppm: −38.58 s.

EXAMPLE 15

A) 1,3-Dimethyl-2-fluoroimidazolidinium bis(trifluoromethyl)imide

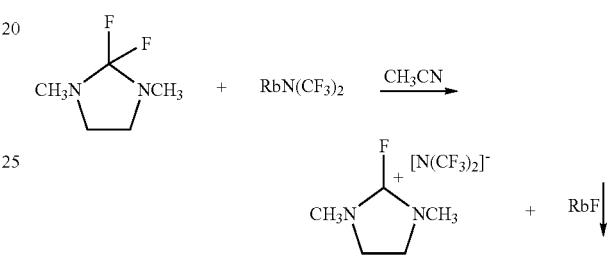

A solution of 0.46 g (3.37 mmol) of 1,3-dimethyl-2,2-difluoroimidazolidine in 4.57 g of dry acetonitrile is added with stirring at room temperature to a solution of 0.73 g (3.10 mmol) of RbN(CF$_3$)$_2$, prepared from the reaction of 0.32 g of RbF with 0.96 g of trifluoromethanesulfonyl fluoride, known from EP 1081129 B1, in 7 ml of dry acetonitrile. 1,3-Dimethyl-2,2-difluoroimidazolidine was obtained analogously to the description from A. A. Kolomeitcev et al., J. of Fluorine Chem. 103 (2000)159-162 by reaction of 1,3-dimethyl-2,2-dichloroimidazolidine with KF in acetonitrile. The reaction mixture is stirred for 30 minutes, and RbF is subsequently filtered off under a protective-gas atmosphere and washed a number of times with 3 ml of dry acetonitrile. The solvent is distilled off under reduced pressure at 0° C. and dried, giving 1,3-dimethyl-2-diethylaminoimidazolidinium bis(trifluoromethyl)imide.

$^1$H NMR (reference: TMS internal; CD$_3$CN), ppm: 2.96 br. s (2CH$_3$), 3.87 br. s (2CH$_2$).

$^{19}$F NMR (reference: CCl$_3$F internal; CD$_3$CN), ppm: −36.42 s (2CF$_3$), −53.74 s (CF).

B) 1,3-Dimethyl-2-diethylaminoimidazolidinium bis(trifluoromethyl)imide

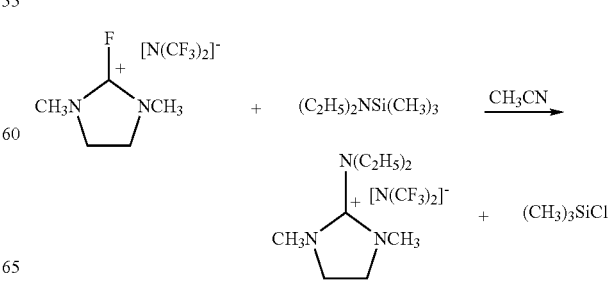

0.50 g (3.44 mmol) of N,N-diethyltrimethylsilylamine are added over the course of 5 minutes with ice-cooling to a solution of 0.83 g (3.10 mmol) of 1,3-dimethyl-2-fluoroimidazolidinium bis(trifluoromethyl)imide in 10 ml of dry acetonitrile. The reaction mixture is stirred for 30 minutes at 0° C. and subsequently brought to room temperature. The volatile constituents are distilled off under reduced pressure, and the residue is dried under reduced pressure at 7.0 Pa and room temperature, giving 0.59 g of 1,3-dimethyl-2-diethylaminoimidazolidinium bis(trifluoromethyl)imide, corresponding to a yield of 59.4%.

$^1$H NMR (reference: TMS internal; CD$_3$CN), ppm: 1.13 t (2CH$_3$), 2.91 s (2CH$_3$), 3.30 q (2CH$_2$), 3.66 s (2CH$_2$), $^3J_{H,H}$=7.1 Hz.

$^{19}$F NMR (reference: CCl$_3$F internal; CD$_3$CN), ppm: −35.96 s (2CF$_3$).

EXAMPLE 16

A) 1,3-Dimethyl-2-chloroimidazolidinium bis(fluorosulfonyl)imide

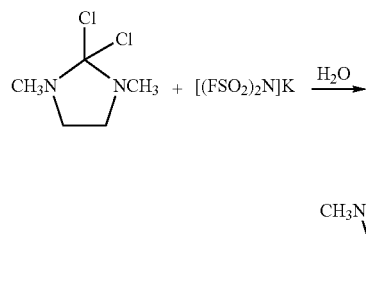

A solution of 3.9 g (17.8 mmol) of potassium bis(fluorosulfonyl)imide in 20 ml of water is added with stirring at room temperature to a solution of 3.0 g (17.7 mmol) of 1,3-dimethyl-2,2-dichloroimidazolidine in 15 ml of water. The reaction mixture is stirred for 30 minutes, and the residue is subsequently filtered off, washed with 20 ml of water and dried under reduced pressure at 7 Pa and 60° C., giving 5.15 g of 1,3-dimethyl-2-chloroimidazolidinium bis(fluorosulfonyl)imide, corresponding to a yield of 92.7%.

m.p.: 129-130° C.

$^1$H NMR (reference: TMS internal; CD$_3$CN), ppm: 3.13 s (2CH$_3$), 3.94 s (2CH$_2$).

$^{19}$F NMR (reference: CCl$_3$F internal; CD$_3$CN), ppm: 52.38 s (2SO$_2$F).

B) 1,3-Dimethyl-2-diethylaminoimidazolidinium bis(fluorosulfonyl)imide

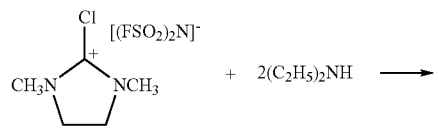

-continued

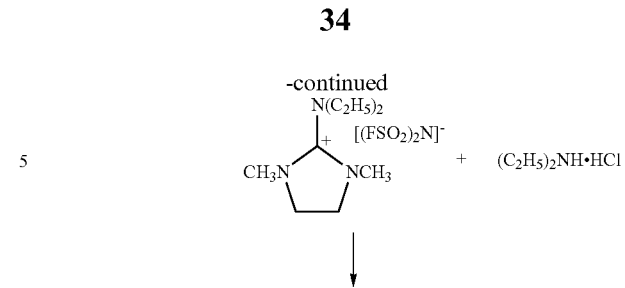

1.4 g (19.14 mmol) of diethylamine are added with stirring at room temperature to 2.0 g (6.38 mmol) of 1,3-dimethyl-2-chloroimidazolidinium bis(fluorosulfonyl)imide. The reaction mixture is stirred for 20 minutes, and 10 ml of water are added. After 5 minutes, the residue is filtered off and washed a number of times with 10 ml of water [lacuna] dried under reduced pressure at 7 Pa and 60° C., giving 2.15 g of 1,3-dimethyl-2-diethylaminoimidazolidinium bis(fluorosulfonyl)imide, corresponding to a yield of 96.2%.

$^1$H NMR (reference: TMS internal; CD$_3$CN), ppm: 1.17 t (2CH$_3$), 2.92 s (2CH$_3$), 3.32 q (2CH$_2$), 3.66 s (2CH$_2$), $^3J_{H,H}$=7.1 Hz.

$^{19}$F NMR (reference: CCl$_3$F internal; CD$_3$CN), ppm: 52.38 s (2SO$_2$F).

EXAMPLE 17

A) Bis(dimethylamino)chlorocarbenium methylsulfate

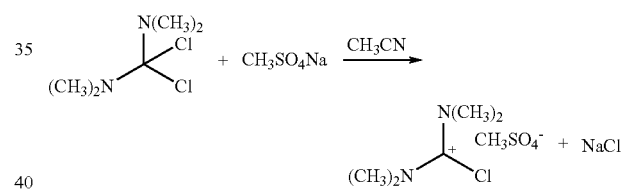

1.54 g (11.48 mmol) of sodium methylsulfate and 10 ml of dry acetonitrile are added under an inert-gas atmosphere to 1.96 g (11.46 mmol) of bis(dimethylamino)dichloromethane. The reaction mixture is stirred for 5 hours at room temperature, and the precipitate of NaCl is filtered off. The solvent of the filtrate is subsequently distilled off, and the residue obtained is dried for 1 hour at an oil-bath temperature of 50° C. under reduced pressure at 7.0 Pa, giving 2.78 g of bis(dimethylamino)chlorocarbenium methylsulfate as a viscous liquid, corresponding to a yield of 98.3%.

$^1$H NMR (reference: TMS internal; acetonitrile-D$_3$), ppm: 3.28 s (4CH$_3$), 3.62 s (CH$_3$).

B) Hexamethylguanidinium methylsulfate

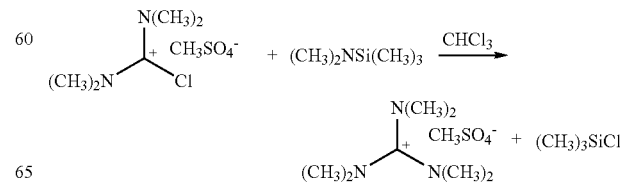

10 ml of dry chloroform and 1.29 g (11.00 mmol) of N,N-dimethyltrimethylsilylamine are added to 2.45 g (9.93 mmol) of bis(dimethylamino)chlorocarbenium methylsulfate. The reaction mixture is stirred for 1 hour at room temperature, and all volatile compounds are subsequently removed under reduced pressure. The residue is dried for a further 1 hour under reduced pressure at 7.0 Pa and an oil-bath temperature of 50° C., giving 2.42 g of hexamethylguanidinium methylsulfate, corresponding to a yield of 95.5%.

m.p.: 187-188° C.

$^1$H NMR (reference: TMS internal; acetonitrile-$D_3$), ppm: 2.88 s (6$CH_3$), 3.51 s ($CH_3$).

EXAMPLE 18

A) Bis(dimethylamino)chlorocarbenium bis(pentafluoroethyl)phosphinate

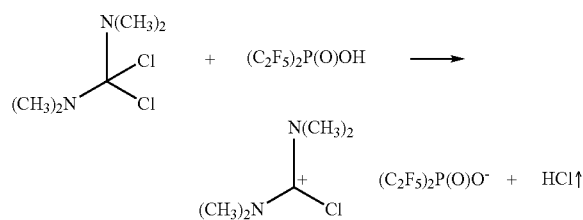

5.88 g (19.47 mmol) of bis(pentafluoroethyl)phosphinic acid are added to 3.33 g (19.47 mmol) of bis(dimethylamino)dichloromethane. The hydrogen chloride formed is removed in a stream of nitrogen. The reaction mixture is stirred at room temperature for 30 minutes, and the residue is dried under reduced pressure at 7 Pa and an oil-bath temperature of 60° C. over the course of 3 hours, giving 8.48 g of bis(dimethylamino)chlorocarbenium bis(pentafluoroethyl)phosphinate as a liquid, corresponding to a yield of 99.7%.

$^1$H NMR (reference: TMS internal; acetonitrile-$D_3$), ppm: 3.27 s (4$CH_3$).

$^{19}$F NMR (reference: $CCl_3F$ internal; acetonitrile-$D_3$), ppm: −80.18 s (2$CF_3$), −124.88 d (2$CF_2$), $^2J_{P,F}$=68 Hz.

$^{31}$P NMR (acetonitrile-$D_3$; standard: 85% $H_3PO_4$ external), ppm: −2.64 quin., $^2J_{P,F}$=68 Hz.

B) Hexamethylguanidinium bis(pentafluoroethyl)phosphinate

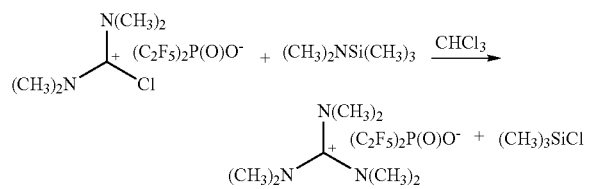

20 ml of dry chloroform and 1.85 g (15.78 mmol) of N,N-dimethyltrimethylsilylamine are added to 6.23 g (14.27 mmol) of bis(dimethylamino)chlorocarbenium bis(pentafluoroethyl)phosphinate. The reaction mixture is stirred for 1 hour at room temperature, and all volatile products are removed under reduced pressure. The residue is subsequently dried at 7.0 Pa and an oil-bath temperature of 50° C. for 1 hour, giving 6.29 g of hexamethylguanidinium bis(pentafluoroethyl)phosphinate, corresponding to a yield of 99%.

m.p.: 45-47° C.

$^1$H NMR (reference: TMS internal; acetonitrile-$D_3$), ppm: 2.88 s (6$CH_3$).

$^{19}$F NMR (reference: $CCl_3F$ internal; acetonitrile-$D_3$), ppm: −80.21 s (2$CF_3$), −124.89 d (2$CF_2$), $^2J_{P,F}$=66 Hz.

$^{31}$P NMR (acetonitrile-$D_3$; standard: 85% $H_3PO_4$ external), ppm: −2.62 quin., $^2J_{P,F}$=66 Hz.

EXAMPLE 19

A) 1,3-Dimethyl-2-chloroimidazolidinium methylsulfate

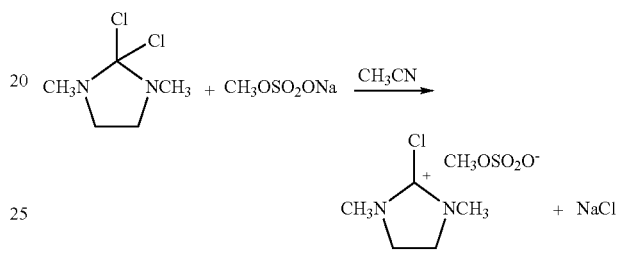

3.00 g (17.75 mmol) of 1,3-dimethyl-2,2-dichloroimidazolidine and 2.38 g (17.75 mmol) of sodium methylsulfate are mixed with 20 ml of dry acetonitrile. The reaction mixture is stirred for 5 hours at room temperature, and the precipitate NaCl is filtered off. The solvent is distilled off, and the residue is dried for 1 hour under a reduced pressure of 7 Pa and at 50° C., giving 4.09 g of 1,3-dimethyl-2-chloroimidazolidinium methylsulfate as a viscous material, corresponding to a yield of 94.2%.

$^1$H NMR (reference: TMS internal; $CD_3CN$), ppm: 3.13 s (2$CH_3$), 3.50 s ($OCH_3$), 3.98 s (2$CH_2$).

B) 1,3-Dimethyl-2-dimethylaminoimidazolidinium methylsulfate

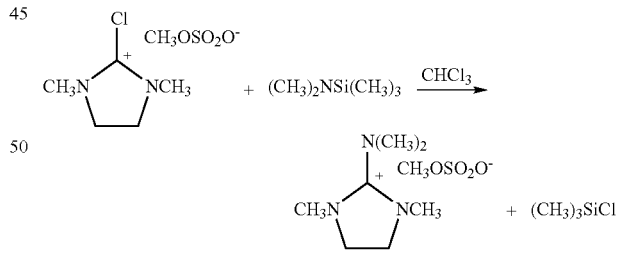

1.33 g (11.34 mmol) of N,N-diethyltrimethylsilylamine are added over the course of 5 minutes at room temperature and with vigorous stirring to 2.50 g (10.22 mmol) of 1,3-dimethyl-2-chloroimidazolidinium methylsulfate in 10 ml of dry chloroform. The solvent is distilled off, and the residue is washed three times with 5 ml of diethyl ether and subsequently dried under a reduced pressure of 7.0 Pa and at 50° C. for 1 hour. The product is crystallised from a mixture of tetrahydrofuran:diethyl ether (1:1), giving 2.22 g of 1,3-dimethyl-2-dimethylaminoimidazolidinium methylsulfate, corresponding to a yield of 85.7%.

m.p.: 124-127° C.

$^1$H NMR (reference: TMS internal; CD$_3$CN), ppm: 2.97 s (2CH$_3$), 2.99 s (2CH$_3$), 3.49 s (OCH$_3$), 3.65 s (2CH$_2$).

EXAMPLE 20

A) 1,3-Dimethyl-2-chloroimidazolidinium dihydrophosphate

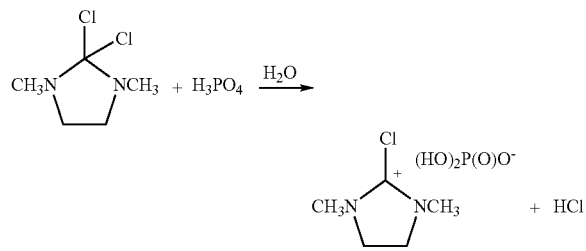

5.0 g (29.58 mmol) of 1,3-dimethyl-2,2-dichloroimidazolidine and 3.41 g of an 85% phosphoric acid (29.58 mmol) are mixed at room temperature. The reaction mixture is stirred for 1 hour at 60° C. All volatile constituents are removed under reduced pressure at 7 Pa and 60° C., giving 6.82 g of 1,3-dimethyl-2-chloroimidazolidinium dihydrophosphate. The yield is approximately quantitative.

$^1$H NMR (reference: TMS internal; D$_2$O), ppm: 2.89 s (2CH$_3$), 3.73 s (2CH$_2$), 4.78 s (OH).

$^{31}$P NMR (D$_2$O; standard: 85% H$_3$PO$_4$ external), ppm: 2.4 s.

B) 1,3-Dimethyl-2-diethylaminoimidazolidinium dihydrophosphate

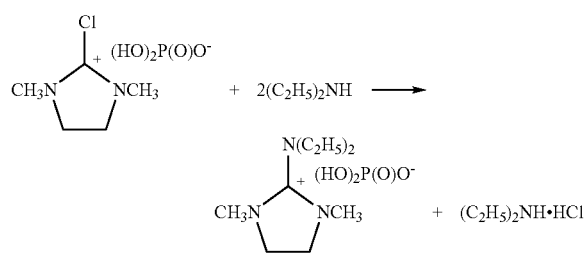

4.26 g (58.24 mmol) of diethylamine and 10 ml of water are added with stirring to 6.70 g (29.06 mmol) of 1,3-dimethyl-2-chloroimidazolidinium dihydrophosphate. The reaction mixture is stirred for a further 10 minutes, and the solution is extracted 9 times with 30 ml of dichloromethane. The extract is dried using magnesium sulfate, and the solvent is distilled off. The residue is dried for 2 hours under reduced pressure at 7 Pa and an oil-bath temperature of 60° C., giving 5.58 g of 1,3-dimethyl-2-diethyl-aminoimidazolidinium dihydrophosphate, corresponding to a yield of 97.6%.

$^1$H NMR (reference: TMS internal; D$_2$O), ppm: 0.97 t (2CH$_3$), 2.76 s (2CH$_3$), 3.16 q (2CH$_2$), 3.50 s (2CH$_2$), 4.73 s (OH), $^3J_{H,H}$=7.2 Hz.

$^{31}$P NMR (D$_2$O; standard: 85% H$_3$PO$_4$ external), ppm: 2.9 s.

EXAMPLE 21

A) 1,3-Dimethyl-2-chloroimidazolidinium dimethylphosphate

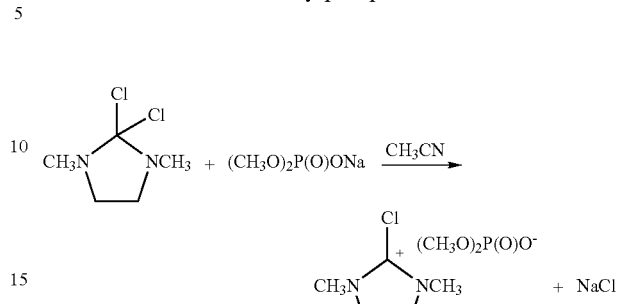

3.00 g (17.75 mmol) of 1,3-dimethyl-2,2-dichloroimidazolidine and 2.63 g (17.77 mmol) of sodium dimethylphosphate are mixed with 20 ml of acetonitrile and 2 ml of water. The reaction mixture is stirred for 12 hours at room temperature, and the precipitate NaCl is subsequently filtered off. The solvent is distilled off, and the residue is dried for 6 hours under a reduced pressure of 7 Pa and at an oil-bath temperature of 70-80° C., giving 4.39 g of 1,3-dimethyl-2-chloroimidazolidinium dimethylphosphate, corresponding to a yield of 95.6%.

$^1$H NMR (reference: TMS internal; CD$_3$CN), ppm: 3.10 s (2CH$_3$), 3.50 d (2OCH$_3$), 3.94 s (2CH$_2$), $^3J_{H,P}$=10.6 Hz.

$^{31}$P NMR (D$_2$O; standard: 85% H$_3$PO$_4$ external), ppm: 7.0 quin., $^3J_{H,P}$=10.5 Hz.

B) 1,3-Dimethyl-2-dimethylaminoimidazolidinium dimethylphosphate

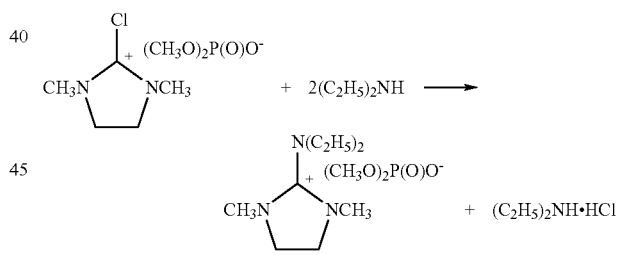

1.14 g (15.59 mmol) of diethylamine and 10 ml of water are added with stirring to 2.0 g (7.73 mmol) of 1,3-dimethyl-2-chloroimidazolidinium dimethylphosphate. The reaction mixture is stirred for 10 minutes at room temperature, and 10 ml of ethanol are subsequently added. The solution is extracted 5 times with 30 ml of dichloromethane. Water is distilled off from the aqueous phase. The residue is dried for 4 hours under a reduced pressure of 7 Pa at an oil-bath temperature of 70-80° C., giving 1.85 g of 1,3-dimethyl-2-dimethylaminoimidazolidinium dimethylphosphate, corresponding to a yield of 81%.

m.p.: 123-125° C.

$^1$H NMR (reference: TMS internal; CD$_3$CN), ppm: 1.10 t (2CH$_3$), 2.89 s (2CH$_3$), 3.30 q (2CH$_2$), 3.50 d (2OCH$_3$), 3.63 s (2CH$_2$), $^3J_{H,P}$=10.7 Hz, $^3J_{H,H}$=7.1 Hz.

$^{31}$P NMR (D$_2$O; standard: 85% H$_3$PO$_4$ external), ppm: 7.0 quin., $^3J_{H,P}$=10.6 Hz.

The invention claimed is:

1. A process for the preparation of guanidinium salts of the formula (1)

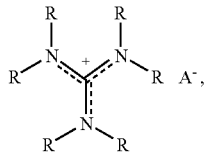

(1)

in which the substituents R in each case, independently of one another, have the meaning of hydrogen,
straight-chain or branched alkyl having 1-20 C atoms,
saturated, partially or fully unsaturated cycloalkyl having 3-7 C atoms, which may be substituted by alkyl groups having 1-6 C atoms,
where one or more substituents R may be partially or fully substituted by halogen or partially by CN or $NO_2$ and halogen denotes F, Cl, Br or I,
where up to four substituents R may be bonded to one another in pairs by a single or double bond
and where a carbon atom or two non-adjacent carbon atoms of one or more substituents R may be replaced by atoms and/or atom groups selected from the group —O—, —C(O)—, —C(O)O—, —S—, —S(O)—, —$SO_2$—, —$SO_3$—, —N=, —N=N—, —NH—, —NR'—, —PR'—, —P(O)R'—, —P(O)R'—O—, —O—P(O)R'—O—, and —P(R')$_2$=N—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and
$A^-$ is a sulfonate, alkyl- or arylsulfate, hydrogensulfate, imide, methanide, carboxylate, phosphate, phosphinate, phosphonate, borate, thiocyanate, perchlorate, fluorosilicate or nitrate,
by reaction of a compound of the formula (2)

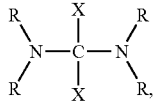

(2)

in which the substituents R have a meaning indicated for formula (1) and X denotes F, Cl or Br,
with a compound of the formula (3)

$Kt^+A^-$        (3), in which $A^-$ has a meaning indicated for formula (1) and $Kt^+$ can be a proton, R"$_3$Si, an alkali or alkaline earth metal cation, an ammonium cation, a phosphonium cation or a cation from group 11 or 12,
where R" in each case, independently of one another, denotes phenyl or a linear or branched alkyl group having 1-6 C atoms, which maybe substituted by phenyl, and subsequent reaction of the resultant compound of the formula (4)

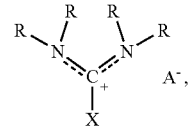

(4)

where the substituents R, X and $A^-$ have a meaning indicated for formula (1) or (2), with compounds of the formula (5)

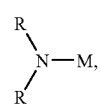

(5)

where the substituents R have a meaning indicated for formula (1) and M denotes hydrogen, R"$_3$Si, an alkali or alkaline earth metal and R" in each case, independently of one another, denotes phenyl or a linear or branched alkyl group having 1-6 C atoms, which may be substituted by phenyl.

2. A process according to claim 1, where a compound of formula $Kt^+A^-$ (3) is employed, in which $Kt^+$ has a meaning indicated in claim 1 and $A^-$ is
$[R^1OSO_3]^-$, $[R^1SO_3]^-$, $[R^FSO_3]^-$, $[(FSO_2)_2N]^-$, $[(R^FSO_2)_2N]^-$, $[(R^FSO_2)(R^FCO)N]^-$, $[(R^FSO_2)_3C]^-$, $[(FSO_2)_3C]^-$, $[R^1CH_2C(O)O]^-$, $[R^FC(O)O]^-$, $[P(C_nF_{2n+1-m}H_m)_yF_{6-y}]^-$, $[P(_6F_5)_yF_{6-y}]^-$, $[(R^1O)_2P(O)O]^-$, $[R^1_2P(O)O]^-$, $[R^1P(O)O_2]^{2-}$, $[R^F_2P(O)O]^-$,$[R^FP(O)O_2]^{2-}$, $[BF_{4-z}R^F_z]^-$, $[BF_{4-z}(CN)_z]^-$, $[B(C_6F_5)_4]^-$, $[B(OR^1)_4]^-$, $[N(CN)_2]^-$, $[C(CN)_3]^-$, $[N(CF_3)_2]^-$, $[HSO_4]^-$, $[SiF_6]^{2-}$, $[ClO_4]^-$ or $[NO_3]^-$, in which the substituents $R^F$ in each case, independently of one another, have the meaning of perfluorinated and straight-chain or branched alkyl having 1-20 C atoms,
perfluorinated and straight-chain or branched alkenyl having 2-20 C atoms and one or more double bonds,
perfluorinated and saturated, partially or fully unsaturated cycloalkyl having 3-7 C atoms, which may be substituted by perfluoroalkyl groups,
where the substituents $R^F$ may be bonded to one another in pairs by a single or double bond and
where a carbon atom or two non-adjacent carbon atoms of the substituent $R^F$ which are not in the α-position to the heteroatom may be replaced by atoms and/or atom groups selected from the group —O—, —C(O)—, —S—, —S(O)—, —$SO_2$—, —N=, —N=N—, —NR'—, —PR'— and —P(O)R'—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle,
in which the substituents $R^1$ in each case, independently of one another, have the meaning of
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where the substituents $R^1$ may be partially substituted by CN, $NO_2$ or halogen and halogen denotes F, Cl, Br or I, where the substituents $R^1$ may be bonded to one another in pairs by a single or double bond and where a carbon atom or two non-adjacent carbon atoms of the substituent $R^1$ which are not in the α-position to the heteroatom may be replaced by atoms and/or atom groups selected from the group —O—, —C(O)—, —C(O)O—, —S—, —SO—, —$SO_2$—, —$SO_3$—, —N=, —N=N—, —NH—, NR'—, —PR'—, —P(O)R'—, P(O)R'O—, OP(O)R'O—, —PR'$_2$=N—, —C(O)NH—, —C(O)NR'—, $SO_2$NH— or —$SO_2$NR'—, where R' denotes non-fluorinated, partially or perfluorinated alkyl having 1-6 C atoms, saturated or partially unsaturated cycloalkyl having 3-7 C atoms, unsubstituted or substituted phenyl or an unsubstituted or substituted heterocycle and the variables n denotes 1 to 20, m denotes 0, 1, 2, or 3, y denotes 0, 1, 2, 3 or 4, and z denotes 0, 1, 2, 3 or 4.

3. A Process according to claim 1, wherein $A^-$ is $[CH_3OSO_3]^-$, $[C_2H_5OSO_3]^-$, $[C(CN)_3]^-$, $[CH_3SO_3]^-$, $[C_8H_{17}SO_3]^-$, $[CH_3C_6H_4SO_3]^-$, $[CF_3SO_3]^-$, $[C_2H_5SO_3]^-$, $[CF_3CF_2SO_3]^-$, $[(CF_3SO_2)_2N]^-$, $[(FSO_2)_2N]^-$, $[(CF_3SO_2)(CF_3CO)N]^-$, $[(C_2F_5SO_2)(CF_3CO)N]^-$, $[(C_2F_5SO_2)_2N]^-$, $[(CF_3SO_2)_3C]^-$, $[(C_2F_5SO_2)_3C]^-$, $[(FSO_2)_3C]^-$, $[CH_3C(O)O]^-$, $[C_2H_5C(O)O]^-$, $[CF_3C(O)O]^-$, $[CF_3CF_2C(O)O]^-$, $[PF_6]^-$, $[P(C_2F_5)_3F_3]^-$, $[P(C_4F_9)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_2F_5)_2F_4]^-$, $[(HO)_2P(O)O]^-$, $[(CH_3O)_2P(O)O]^-$, $[(CH_3O)_2P(O)O]^-$, $[(C_2F_5)_2P(O)O]^-$, $[(C_2F_5)P(O)O_2]^{2-}$, $[P(C_6F_5)_2F_4]^-$, $[(CH_3)_2P(O)O]^-$, $[CH_3P(O)O_2]^{2-}$, $[(CF_3)_2P(O)O]^-$, $[CF_3P(O)O_2]^{2-}$, $[BF_4]^-$, $[BF_3(CF_3)]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CN)_4]^-$, $[B(OCH_3)_4]^-$, $[B(CF_3)_4]^-$, $[B(OCH_3)_2(OC_2H_5)_2]^-$, $[B(O_2C_2H_4)_2]^-$, $[B(O_2C_2H_2)_2]^-$, $[B(O_2C_6H_4)_2]^-$, $[N(CN)_2]^-$, $[N(CF_3)_2]^-$, $[HSO_4]^-$, $[ClO_4]^-$, $[SiF_6]^-$, $[SCN]^-$ or $[NO_3]^-$.

4. A process according to claim 1, wherein the substituent X in dihalogen compounds of the formula (2) according to claim 1 denotes fluorine or chlorine.

5. A process according to claim 1, wherein the substituent R in compounds of the formula (5) according to claim 1 in each case, independently of one another, has the meaning of hydrogen, straight-chain or branched alkyl having 1-20 C atoms or saturated, partially or fully unsaturated cycloalkyl having 3-7 C atoms, which may be substituted by alkyl groups having 1-6 C atoms.

6. A process according to claim 1, wherein the first step of the process is carried out in water.

7. A process according to one claim 1, wherein the first step of the process is carried out at temperatures of 0° to 150° C.

8. A process according to claim 1, wherein the first step of the process is carried out in an organic solvent.

9. A process according to claim 1, wherein the first step of the process carried out at temperatures of −50° to 150° C.

10. A process according to claim 1, wherein the second step of the process is carried out without a solvent.

11. A process according to claim 1, wherein the second step of the process is carried out at a temperature at which at least one component is liquid.

12. A process according to claim 1, wherein the second step of the process is carried out in an organic solvent.

13. A process according to claim 1, wherein the second step of the process is carried out at temperatures of 50° to 150° C.

14. A process according to claim 1, wherein the second step of the process is carried out in water.

15. A process according to claim 1, wherein the second step of the process is carried out at temperatures of 0° to 150° C.

16. A compound that is:

1,3-dimethyl-2-chloroimidazolidinium tris(pentafluoroethyl)trifluorophosphate, bis(dimethylamino)chlorocarbenium, tris(pentafluoroethyl)trifluorophosphate, bis(dimethylamino)chlorocarbenium bis(trifluoromethanesulfonyl)imide, bis(dimethylamino)chlorocarbenium trifluoromethanesulfonate, 1,3-dimethyl-2-chloroimidazolidinium trifluoromethanesulfonate, bis(dimethylamino)chlorocarbenium tosylate, bis(dimethylamino)chlorocarbenium hydrogensulfate, 1,3-dimethyl-2-chloroimidazolidinium nitrate, bis(dimethylamino)chlorocarbenium trifluoroacetate, bis(dimethyiamino)chlorocarbenium thiocyanate, bis(dimethylamino)chlorocarbenium tetracyanoborate, 1,3-dimethyl-2-diethylamninoimidazolidinium bis(trifluoromethyl)imide, 1,3-dimethyl-2-chloroimidazolidinium bis(fluorosulfonyl)imide bis(dimethylamino)chlorocarbenium methylsulfate, bis(dimethylamino)chlorocarbenium bis(pentafluoroethyl)phosphinate, 1,3-dimethyl-2-chloroimidazolidinium methylsulfate, 1,3-dimethyl-2-chloroimidazolidinium dihydrophosphate, or 1,3-dimethyl-2-chloroimidazolidinium dimethylphosphate.

* * * * *

UNITED STATES PATENT AND TRADEMARK OFFICE
CERTIFICATE OF CORRECTION

PATENT NO. : 7,439,395 B2
APPLICATION NO. : 10/588190
DATED : October 21, 2008
INVENTOR(S) : Ignatyev et al.

It is certified that error appears in the above-identified patent and that said Letters Patent is hereby corrected as shown below:

Column 40, line 34 reads " $F_{2n+1-m}H_m)_yF_{6-y}]^-$, $[P(_6F_5)_yF_{6-y}]^-$, $[(R^1O)_2P(O)O]^-$," should read -- $F_{2n+1-m}H_m)_yF_{6-y}]^-$, $[P(C_6F_5)_yF_{6-y}]^-$, $[(R^1O)_2P(O)O]^-$, --.

Column 40, line 38 reads "$[HSO_4]^-$, $[SiF_6]^{2-}$, $[ClO_4]^-$ or $[NO_3]^-$," should read -- $[HSO_4]^-$, $[SiF_6]^{2-}$, $[ClO_4]^-$, $[SCN]^-$ or $[NO_3]^-$, --.

Signed and Sealed this

Twenty-sixth Day of January, 2010

David J. Kappos
*Director of the United States Patent and Trademark Office*